United States Patent
Ichimura et al.

(10) Patent No.: US 7,574,034 B2
(45) Date of Patent: Aug. 11, 2009

(54) METHOD FOR JUDGING GRAPHITE TEXTURE IN GRAY CAST IRON, JUDGING PROGRAM RECORDING MEDIUM AND JUDGING SYSTEM

(75) Inventors: Hajime Ichimura, Tochigi (JP); Masanori Imasaki, Tochigi (JP); Tetsuro Aoki, Tochigi (JP); Kunihiro Masuo, Gunma (JP)

(73) Assignee: Kiriu Corporation, Kiryu-shi (JP)

( * ) Notice: Subject to any disclaimer, the term of this patent is extended or adjusted under 35 U.S.C. 154(b) by 860 days.

(21) Appl. No.: 10/517,229

(22) PCT Filed: Dec. 25, 2003

(86) PCT No.: PCT/JP03/16803
§ 371 (c)(1),
(2), (4) Date: Dec. 8, 2004

(87) PCT Pub. No.: WO2004/061431
PCT Pub. Date: Jul. 22, 2004

(65) Prior Publication Data
US 2005/0175232 A1    Aug. 11, 2005

(30) Foreign Application Priority Data
Dec. 27, 2002  (JP) .............................. 2002-379728

(51) Int. Cl.
*G06K 9/00* (2006.01)
*H04N 7/18* (2006.01)
(52) U.S. Cl. ........................................ 382/141; 348/86
(58) Field of Classification Search ........................ None
See application file for complete search history.

(56) References Cited

U.S. PATENT DOCUMENTS 4,333,512 A * 6/1982 Sugiura et al. ............... 164/453

(Continued)

FOREIGN PATENT DOCUMENTS

JP         54-150194 A        11/1979

(Continued)

OTHER PUBLICATIONS

Fairbanks et al., "The Effects of Adding Ultrasound During the Production of Nodular Cast Iron," Ultrasonics Symposium Proceedings, IEEE, 1974, pp. 664-666.*

(Continued)

*Primary Examiner*—Charles Kim
(74) *Attorney, Agent, or Firm*—Foley & Lardner LLP

(57) ABSTRACT

There is provided a method for quantitatively evaluating properties of a graphite structure of a gray cast iron based on a number and a thick and thin degree of graphite components in the structure. In particular, only non-spherical graphite pieces having an average size of 5 μm or more are extracted from a preprocessed image of the graphite structure, and counted (Step S5 of FIG. 3). Further, only graphite pieces having a maximum length of 50 μm or more and less than 150 μm are selected therefrom, and a length and an area of each selected graphite piece are measured (Step S6). An area of an assumptive representative graphite piece having a maximum length (a maximum size) of 100 μm is calculated from these data, and divided by the length 100 μm, to obtain the thick and thin degree (Step S7). The thick and thin degree is shown with the number of the graphite pieces (Step S8).

14 Claims, 24 Drawing Sheets

DIVISION OF GRAPHITE PIECES INTO THOSE OF MAXIMUM SIZE OF LESS THAN 10μm AND THOSE OF MAXIMUM SIZE OF 10μm OR MORE

U.S. PATENT DOCUMENTS 6,126,713 A * 10/2000 Igarashi et al. ................ 75/305

FOREIGN PATENT DOCUMENTS

| JP | 5-273200 A | 10/1993 |
| JP | 11-304736 A | 11/1999 |
| JP | 2000-9668 A | 1/2000 |
| JP | 2002162348 A | 6/2002 |
| JP | 2002-317237 A | 10/2002 |

OTHER PUBLICATIONS

Hideo Nakae et al., "Influence of Graphite Morphology on Fractured Surface in Flake Graphite Cst Iron Measured by Laser Roughness Meter", Chuzo Kogaku, Japan Foundry Engineering Society, 2002, pp. 644-649, vol. 74, No. 10.

Kenji Ishimima et al., "Gazo Joho Shori System ni yoru Kinzoku Sozai no Teiryoka ni Kansuru Kenkyu (second report)" Tochigi-ken Kogyo Shiken Kenkyu Kikan Kenkyu Shuroku, Oct. 1989, vol. 1988, pp. 230-237.

Kenji Ishijima et al., "Gazo Joho Shori System ni yoru Kinzoku Sozai no Teiryoka ni Kansuru Kenkyu (first report)", Tochigi-ken Kogyo Shiken Kenkyu Kikan Kenkyu Shuroku, Jan. 1989, vol. 1987, pp. 171-178.

Harumi Ueno, et al., "Gazo Joho Shori System ni yoru Soshiki no Teiryoka ni Kansuru Kenkyu Kinzoku, Kinzokukei Fukugo Zairyo Soshiki no Teiryoka ni Kansuru Kenkyu", Tochigi-ken Kogyo Gijutu Center Kenkyu Hokoku, Aug. 1991, vol. 1990, pp. 51-59.

H.Y. Yuan et al., "Computer image evaluation of graphite forms in cast iron", Int. J. Cast Metals Res., 1999, vol. 11, pp. 447-451.

* cited by examiner

STEPS OF IMAGE ANALYSIS FOR MEASURING GRAPHITE SPHEROIDIZING RATIO

FIG. 5

| RECORD OF GRAPHITE SPHEROIDIZING RATIO MEASUREMENT | | | |
|---|---|---|---|
| MEASUREMENT DATE 2002/03/29<br><FULL FIELD MEASUREMENT> | | | |
| GRAPHITE PIECES HAVING MAXIMUM SIZE OF 20 MICRONS OR LESS WERE EXCEPTED | | | |
| GRAPHITE STRUCTURE | STRUCTURES I TO IV | STRUCTURES V TO VI | GRAPHITE SPHEROIDIZING RATIO (%) |
| COEFFICIENT | 0 | 1.0 | |
| MEASUREMENT FIELD 1 | 109 | 1 | 0.9 |
| MEASUREMENT FIELD 2 | 112 | 0 | 0.9 |
| MEASUREMENT FIELD 3 | 109 | 1 | 0.9 |
| MEASUREMENT FIELD 4 | * | * | * |
| MEASUREMENT FIELD 5 | * | * | * |
| TOTAL FIELD | 330 | 2 | 0.6 |

<STRUCTURE VIEW>

OUTPUT OF IMAGE ANALYSIS RESULT

MAXIMUM SIZE AND AVERAGE SIZE FOR MEASURING GRAPHITE SIZE

NUMBERS OF DETECTED GRAPHITE PIECES
OF DIFFERENT SHAPES AND SIZES

LINKAGE OF A PLURALITY OF GRAPHITE PIECES INCREASED AMONG GRAPHITE PIECES WITH SIZE OF APPROXIMATELY 150 μm OR MORE

INDICATION OF THICK AND THIN DEGREE OF GRAPHITE PIECES BASED ON THICKNESS OF CALCULATIONAL, ASSUMPTIVE, REPRESENTATIVE GRAPHITE PIECE WITH LENGTH OF 100μm

IMPROVEMENT OF DISC ROTOR GRAPHITE STRUCTURE
BY RATIONALIZING MOLTEN METAL TREATMENT

US 7,574,034 B2

METHOD FOR JUDGING GRAPHITE TEXTURE IN GRAY CAST IRON, JUDGING PROGRAM RECORDING MEDIUM AND JUDGING SYSTEM

TECHNICAL FIELD

The present invention relates to a method capable of analyzing an image of a flake graphite structure, a eutectic graphite structure, or a mixture thereof of a gray cast iron to numerically evaluate intrinsic properties of the graphite structure such as shape (length, thickness, etc.), distribution, and density of the graphite pieces quantitatively, easily, and accurately, and further to a recording medium storing a program for carrying out the method and an evaluation system.

BACKGROUND ART

Known technologies in this field are described, for example, in JP-A-2002-162348, and Hideo Nakae and two others, *Reza Henikei o Mochiita Henjo Kokuen Chutetsu no Hamen Kaiseki ni yoru Kokuen Keitai no Hantei* (Evaluation of graphite shape by fracture surface analysis of graphite cast iron using laser displacement meter), *Chuzo Kogaku*, Japan Foundry Engineering Society, Vol. 74, 2002, No. 10, Pages 644-649. The conventional technologies comprise basic steps of irradiating a fracture surface of a cast iron with a laser light, measuring the surface roughness of the fracture surface, and evaluating shape, distribution, etc. of graphite pieces contained in the structure based on the surface roughness.

The above conventional technologies are the most promising methods in practical use among the known graphite structure evaluation methods. However, in the technologies, a resultant graph must be directly read to obtain final evaluation results, whereby the technologies are disadvantageous in that there are often differences between individuals in the results and that it is difficult to imagine the graphite structure by the results, thus there being still room for improvement.

DISCLOSURE OF INVENTION

The present invention has been completed in view of the above object to provide a technology capable of evaluating a graphite structure of a gray cast iron in numerical terms, quantitatively, easily, and accurately, particularly by efficiently using a known image analysis apparatus such as a graphite spheroidizing ratio measuring apparatus.

Various graphite structures in gray cast irons are identified based on shape, size, length, number, and thickness of graphite pieces, density and orientation of distribution of the graphite pieces, etc. The state of the graphite structure is closely related with the number of the graphite pieces forming the structure, and therefore, the state of the graphite structure can be estimated when the number of the graphite pieces is obtained.

The gray cast iron is generally an iron alloy containing 3 to 4% of carbon and 2 to 3% of silicon, and has a structure of the graphite pieces with various shape and size dispersed in an iron matrix. When a cast iron is solidified, carbon in the cast iron is converted into graphite carbon, combined carbon forming cementite, and a trace of carbon forming a solid solution with the iron matrix. The graphite pieces, which can be observed by examining a polished cast iron sample using a microscope, are composed of the graphite carbon. The cementite can be visually observed in pearlite when the polished sample is corroded. The graphite structure of the cast iron depends on the state of the graphite carbon and the combined carbon with disregard to the trace solid solution carbon, which cannot be visually observed.

In the case of a gray cast iron having a thickness of 10 to 30 mm, the ratio of the combined carbon is generally within a range of approximately 0.4 to 0.9%, and the amount of the combined carbon is hardly changed even when the total carbon amount is increased. Thus, a value calculated by subtracting the amount of the combined carbon from the total carbon amount is the amount of the graphite carbon. The amount of the graphite carbon is increased with increase of the total carbon amount, and as a result, the area ratio of the graphite pieces in the iron matrix increases.

The shape and distribution of the graphite carbon formed in the solidifying process depend mainly on conditions of mixing a matrix metal, melting, teeming, a molten metal treatment, and molding. The graphite structure is significantly changed depending on the conditions even if the chemical composition is not modified. As a general tendency, the graphite pieces are grown to have a large length in thick portions solidified at a low rate, and the graphite pieces are insufficiently grown to be short in thin portions and molten metal stagnant portions solidified at a high rate.

Meanwhile, since the amount of the graphite carbon is constant, a carbon amount of each graphite piece becomes larger and the number of the graphite pieces becomes smaller as the graphite pieces are longer. On the other hand, the number of the graphite pieces becomes larger as the graphite pieces are shorter.

Accordingly, the invention has been achieved based on an assumption that the state of the graphite structure is closely related with the number of the graphite pieces forming the structure.

An aspect of the invention described in claim 1 is a method for quantitatively evaluating a graphite structure of a gray cast iron by an image analysis apparatus, characterized by comprising the steps of analyzing a magnified image of the graphite structure, thereby extracting non-spherical graphite pieces of a particular size class contained in the graphite structure to calculate the number and areas of the non-spherical graphite pieces; calculating a thick and thin degree expressing a degree of thickness of the non-spherical graphite pieces based on the number and the areas; and outputting the number and the thick and thin degree of the non-spherical graphite pieces in combination as an evaluation result.

The magnified image for the image analyzing step may be taken from a microscopic screen image of the graphite structure by an image pickup device (CCD) such as a video camera and a digital camera as described in claim 2. Further, the magnified image may be an image taken by a still camera, which may be read by a scanner, etc., in some cases.

As described in claim 3, the non-spherical graphite pieces may be extracted to calculate the number thereof based on a diameter of a circle having an area equal to that of each graphite piece or on a maximum length of each graphite piece. It is preferred that the smallest graphite piece of the non-spherical graphite pieces extracted to calculate the number thereof has a size of an area equal to that of a circle having a diameter of 5 μm or a maximum length of 10 μm as described in claim 4. It is more preferred that the smallest graphite piece of the non-spherical graphite pieces extracted to calculate the number thereof has a size of an area equal to that of a circle having a diameter of 5 μm as described in claim 5.

In this case, it is preferred from the viewpoint of improving evaluation accuracy that, as described in claim 6, the magnified image is preprocessed to except and eliminate graphite pieces in contact with a frame of the magnified image before extracting the non-spherical graphite pieces of the particular size class, and the number of the extracted non-spherical graphite pieces is corrected by the steps of counting the graphite pieces to be excepted and eliminated; classifying graphite pieces other than the graphite pieces to be excepted and eliminated into a plurality of size classes containing the particular size class, to count a number of the other graphite pieces of each size class; and distributing the graphite pieces to be excepted and eliminated into the size classes proportionally based on a ratio between the numbers of the other graphite pieces, to add a number of the distributed graphite pieces to the numbers of the other graphite pieces.

Further, as described in claim 7, the total area of the extracted non-spherical graphite pieces may be divided by the total number thereof to obtain the thick and thin degree. It is more preferred that graphite pieces having a maximum length of 50 μm or more and less than 150 μm are selected from the extracted non-spherical graphite pieces, maximum lengths and areas of the selected graphite pieces are measured, and an area of a graphite piece having a maximum length of 100 μm is calculated based on the measured data and divided by 100, to obtain the thick and thin degree of a representative graphite piece of the graphite structure as described in claim 8.

An aspect of the invention described in claim 9 is a computer-readable recording medium such as a CD-ROM and a flexible disk, which stores a program for carrying out the steps described in any one of claims 1 to 8.

Further, an aspect of the invention described in claim 10 is a system for quantitatively evaluating a graphite structure of a gray cast iron by image analysis. As shown in FIG. 2, the system comprises an image analysis unit 1, an image input unit 2 for inputting a magnified image of the graphite structure into the image analysis unit 1, and a display unit 3 for indicating an analysis result. The system is characterized in that the image analysis unit 1 comprises a graphite piece number/area calculating unit 4 for analyzing the magnified image of the graphite structure, thereby extracting non-spherical graphite pieces of a particular size class contained in the graphite structure to calculate the number and areas of the non-spherical graphite pieces, and a thick and thin degree calculating unit 5 for calculating a thick and thin degree expressing a degree of thickness of the non-spherical graphite pieces based on the number and the areas, and the number and the thick and thin degree of the non-spherical graphite pieces are visually indicated on the display unit 3 in combination as an evaluation result.

In this case, it is preferred in view of the method according to claim 5 that the smallest graphite piece of the non-spherical graphite pieces extracted to calculate the number thereof has a size of an area equal to that of a circle having a diameter of 5 μm as described in claim 11.

Further, it is preferred in view of the method according to claim 6 that the magnified image is preprocessed to except and eliminate graphite pieces in contact with a frame of the magnified image before extracting the non-spherical graphite pieces of the particular size class, and the image analysis unit comprises a unit 13 (FIG. 24) for correcting the number of the extracted non-spherical graphite pieces of the particular size class by the steps of counting the graphite pieces to be excepted and eliminated; classifying graphite pieces other than the graphite pieces to be excepted and eliminated into a plurality of size classes containing the particular size class, to count a number of the other graphite pieces of each size class; and distributing the graphite pieces to be excepted and eliminated into the size classes proportionally based on a ratio between the numbers of the other graphite pieces, to add a number of the distributed graphite pieces to the numbers of the other graphite pieces, as described in claim 12.

It is more preferred in view of the method according to claim 8 that, as described in claim 13, graphite pieces having a maximum length of 50 μm or more and less than 150 μm are selected from the extracted non-spherical graphite pieces, maximum lengths and areas of the selected graphite pieces are measured, and an area of a graphite piece having a maximum length of 100 μm is calculated based on the measured data and divided by 100, to obtain the thick and thin degree of a representative graphite piece of the graphite structure.

Thus, in the invention, the graphite structure can be numerically and quantitatively evaluated based on the number of the graphite pieces and the thick and thin degree related therewith.

According to the invention, the graphite structure can be quantitatively evaluated based on the number of the graphite pieces and the related thick and thin degree, numerically, easily, and accurately. Thus, the invention is advantageous in that highly reliable evaluation results are obtained without differences between individuals and the actual graphite structure can be easily imagined from the evaluation results.

BRIEF DESCRIPTION OF DRAWINGS

FIG. 5 is an explanatory view showing an analysis result example of the graphite spheroidizing ratio measurement of FIG. 4.

BEST MODE FOR CARRYING OUT INVENTION

Figure 1:
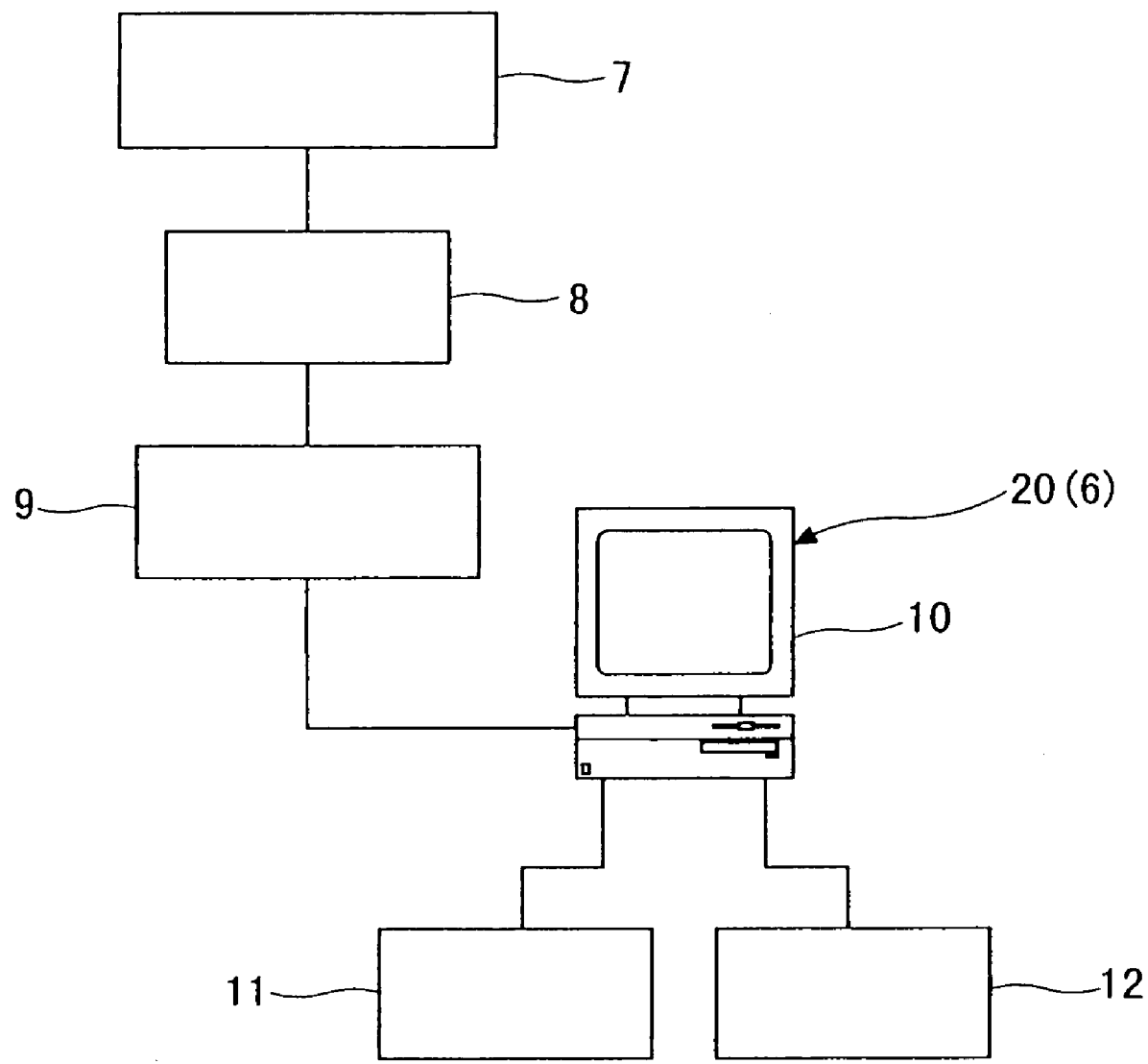
FIG. 1 is an explanatory view schematically showing components of an entire evaluation system according to a preferred embodiment of the present invention.
Figure 2:
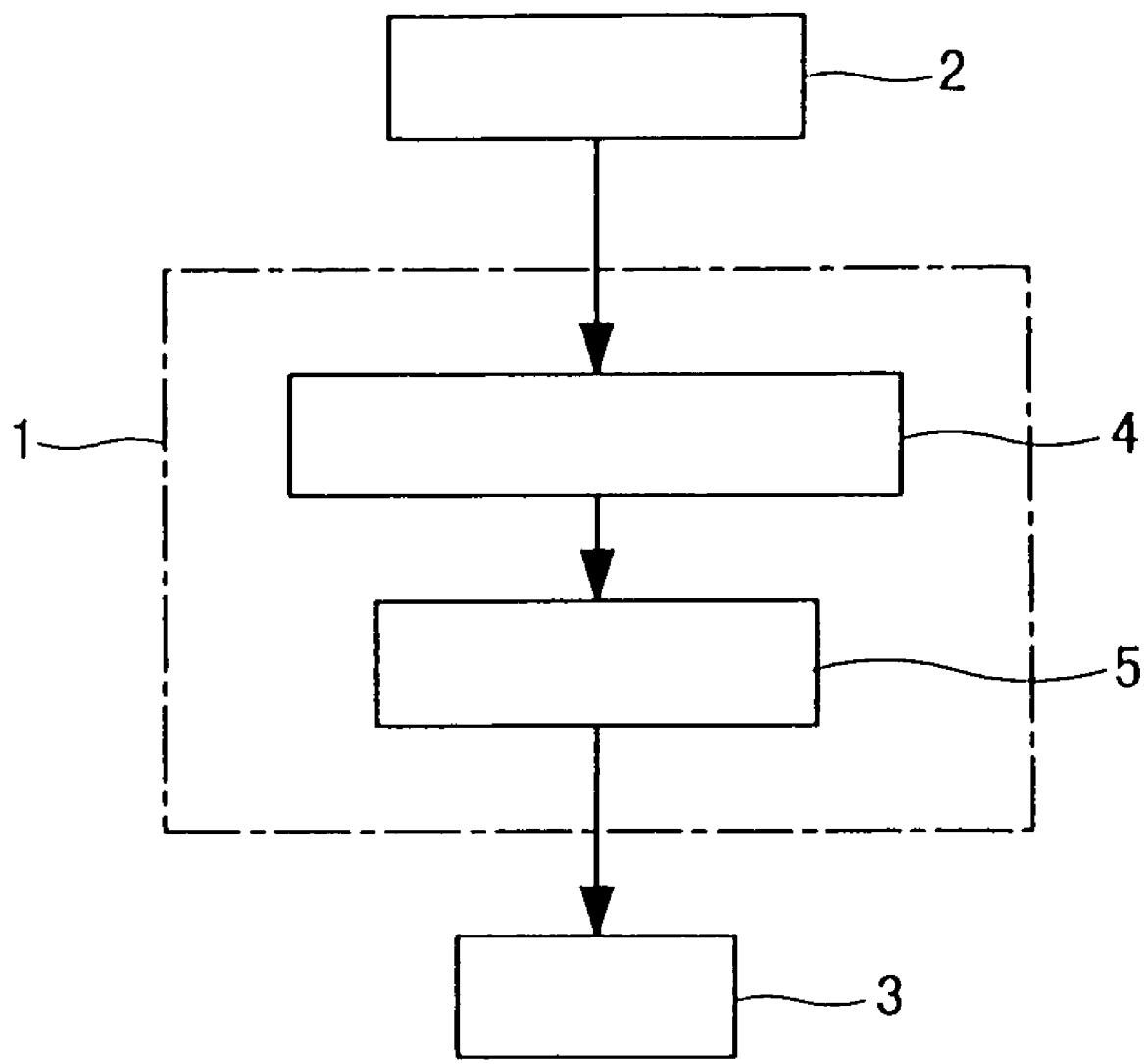
FIG. 2 is a functional block diagram showing a principal part of FIG. 1.
Figure 3:
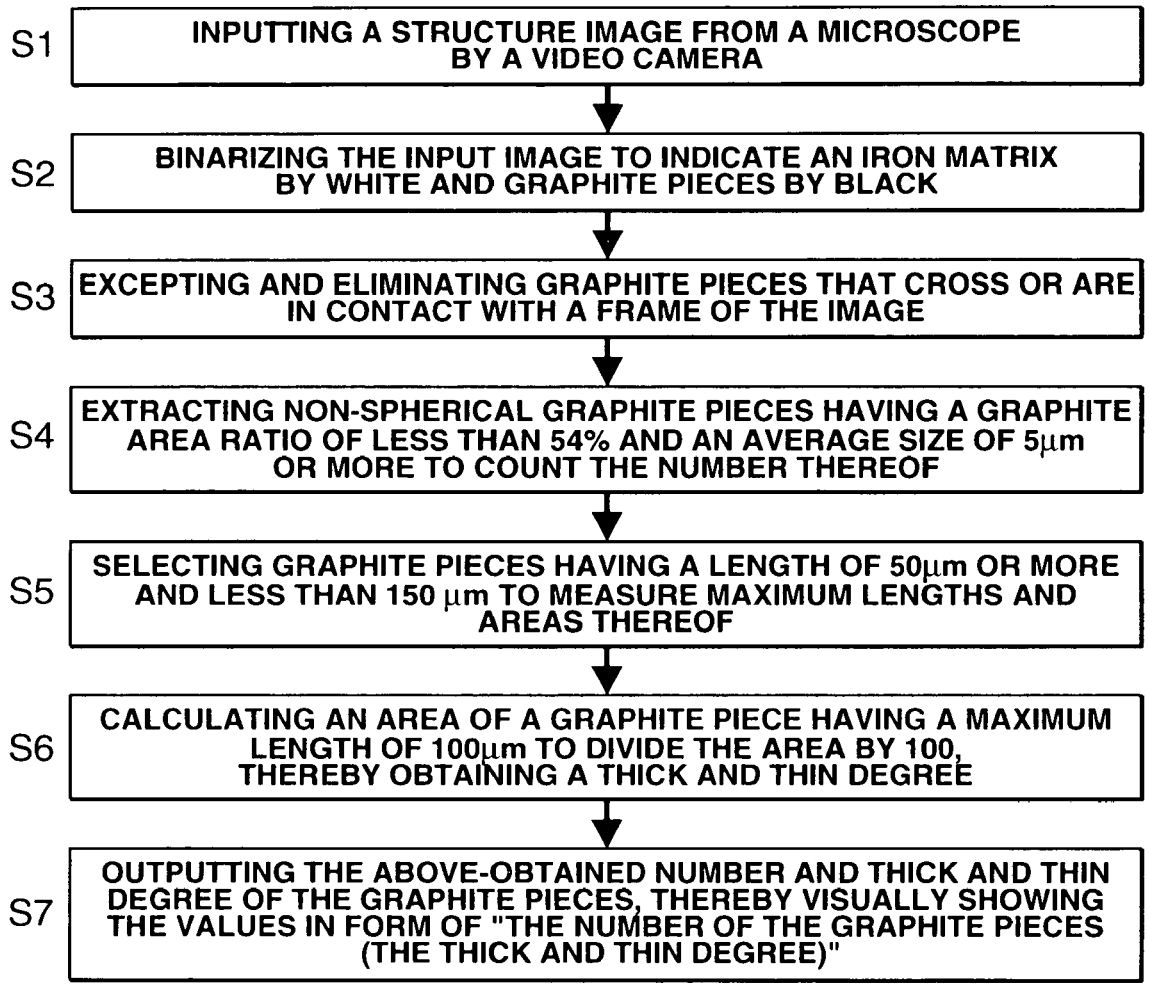
FIG. 3 is a flowchart showing steps of an evaluation method according to the preferred embodiment of the invention.

FIGS. 1 to 3 show a preferred embodiment of the present invention.

FIG. 1 schematically shows components of an evaluation system of the invention, and FIG. 2 shows a schematic functional block diagram thereof. The system is composed of an image analysis unit 1 of an image analysis apparatus 20 having a personal computer 6 as a main component; an optical metallurgical microscope 7; an image input unit (an image pickup unit) 2 of a CCD camera (a video camera) 8; etc. An image taken by the CCD camera 8 is input into the image analysis apparatus 20 through an input port 9. The personal computer 6 comprises a memory device such as a hard disk in addition to CPU, ROM, and RAM with a previously installed prescribed image analysis software, and further comprises an input unit of a not shown keyboard or mouse, a display unit 3 of a CRT display 10, an output unit of a printer 11, an external memory device 12 such as MO, etc.

An evaluation object graphite structure of a gray cast iron is magnified 100 times by the metallurgical microscope 7, and a magnified microscopic image is taken by the CCD camera 8 and input into the image analysis apparatus 20. For example, 640×480 pixels (picture elements) of the input 100 times magnified microscopic image is subjected to the image analysis. The 640-pixels width of the image frame is distributed on a 640-μm scale, whereby there is a relation of 1 pixel=1 μm.

After the image is input into the image analysis apparatus 20 as shown in Step S1 of FIG. 3, the input image is binarized into bright and dark to indicate an iron matrix by white color and graphite pieces by black color (Step S2). At the same time, graphite pieces that intersect (cross) or are in contact with the frame of the image are eliminated and excepted (Step S3). Then, in Step S4, only non-spherical graphite pieces having a graphite area ratio of less than 54% are extracted and counted.

Figure 6A:
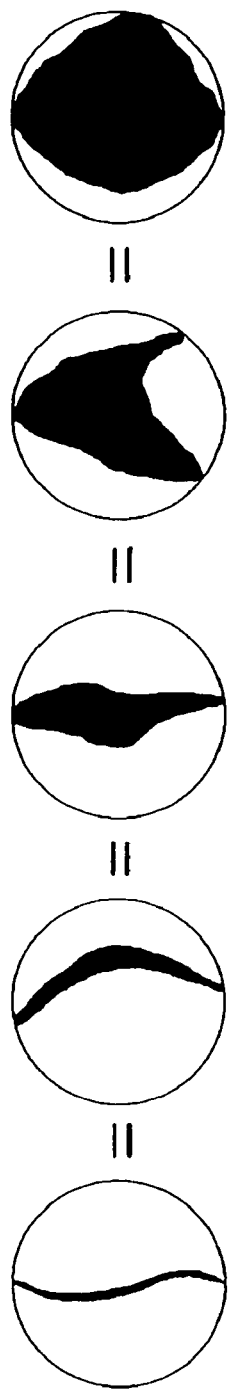
FIG. 6A is an explanatory view of a maximum size method for determining size of graphite pieces.
Figure 6B:
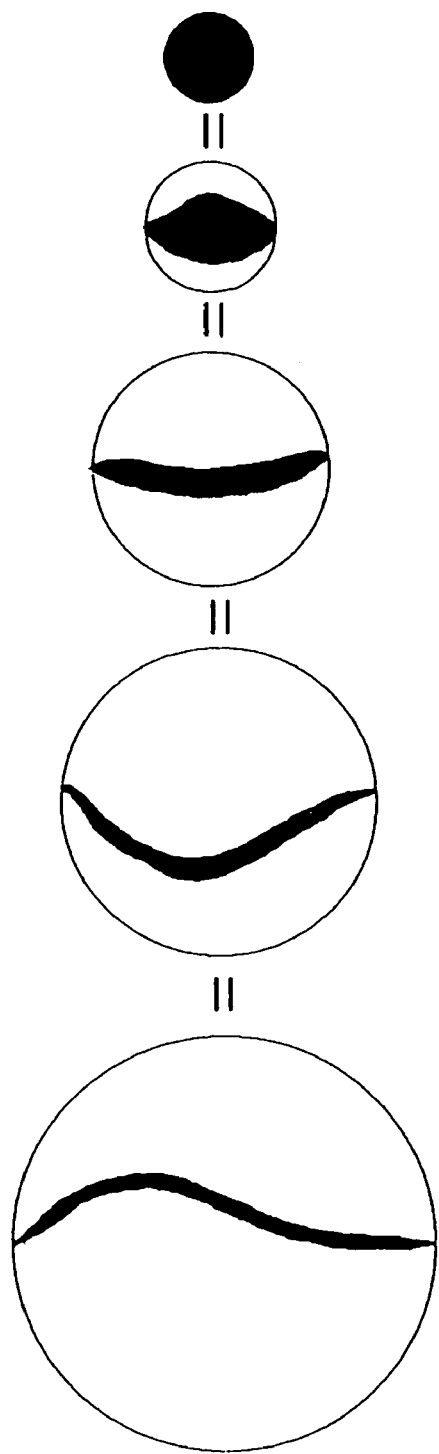
FIG. 6B is an explanatory view of an average size method for determining size of graphite pieces.

In general, two methods shown in FIGS. 6A and 6B may be used for determining size of each graphite piece to be extracted. One is a maximum size method shown in FIG. 6A in which the longest portion of the graphite piece is inscribed in a circle and the diameter of the circle is considered as the size of the graphite piece regardless of the area of the graphite piece. The other is an average size method shown in FIG. 6B in which a diameter of a circle having an area equal to that of the graphite piece is considered as the size of the graphite piece regardless of the length of the graphite piece.

In this embodiment, graphite pieces with an average size of 5 μm or more are extracted. As described above, only the non-spherical graphite pieces having a graphite area ratio of less than 54% and an average size of 5 μm or more are extracted, and the number of the extracted non-spherical graphite pieces is counted and indicated. Graphite pieces with a maximum size (a maximum length) of 10 μm or more may be extracted without the average size method, and only graphite pieces with a maximum size of 10 μm or more and an average size of 5 μm or more may be extracted by using the two methods in combination. An example of a state of an extracted graphite piece structure is shown in the upper left of FIG. 13, the number of the detected graphite pieces being 90 for instance.

It can be assumed from FIG. 13 that the impression of the entire graphite structure largely depends on a degree of thickness of the graphite pieces with a maximum length of 50 μm or more and less than 150 μm (which is referred to as a thick and thin degree in this embodiment as hereinafter described) as shown in the lower left. Based on the assumption, only the graphite pieces having a maximum length of 50 μm or more and less than 150 μm are extracted from the non-spherical graphite pieces, and a maximum size (a maximum length) and an area of each graphite piece are measured (Step S5 of FIG. 3). The measured maximum length and area of each graphite piece are both shown in FIG. 15, and the distribution thereof is shown as a graph in FIG. 16. Then, the median of the graphite piece lengths is obtained and an area of a graphite piece with the median is calculated by using a relational expression shown in FIG. 16.

Figure 16:
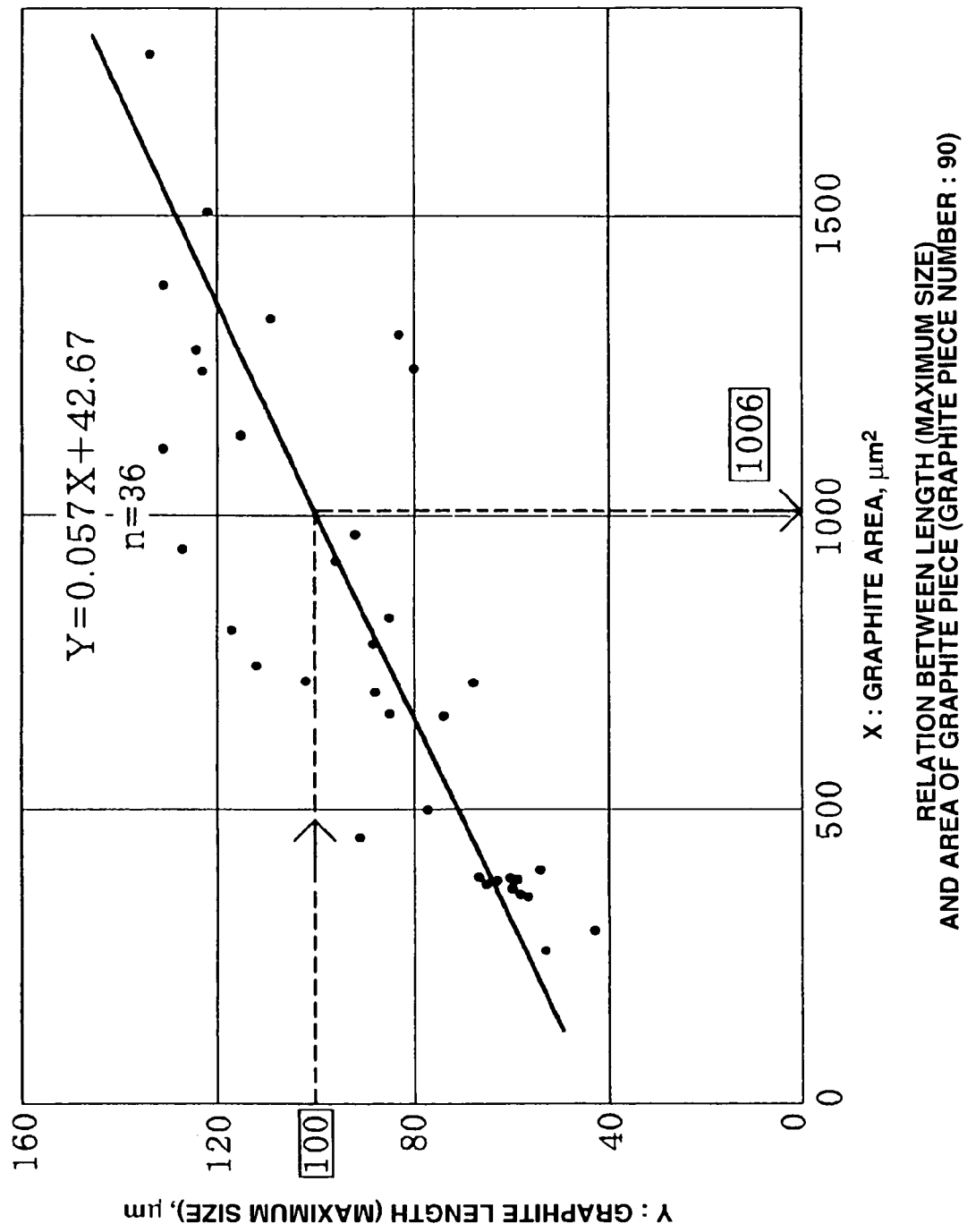
FIG. 16 is a graph showing a relation between the lengths (the maximum sizes) and the areas of the graphite pieces of the structure of FIG. 15.
Figure 17:
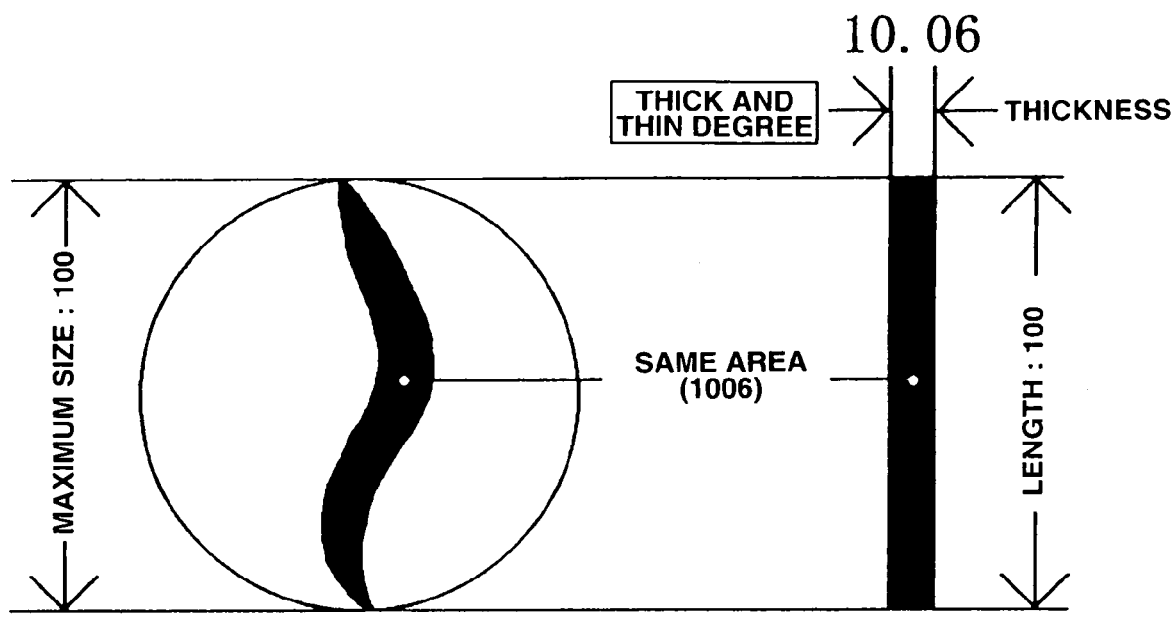
FIG. 17 is an explanatory view of an embodiment of indication of a thick and thin degree of an assumptive, representative graphite piece having a length of 100 μm.

In FIG. 16, the median of lengths 50 to 150 μm is 100 μm, whereby the area of the graphite piece with the median length of 100 μm is 1006 μm². Thus, an assumptive graphite piece with a maximum length (a maximum size) of 100 μm representative of the graphite pieces with a length of 50 μm or more and less than 150 μm is obtained from the shown data, the area of the assumptive graphite piece being 1006 μm². A value of 10.06 is obtained by dividing the area 1006 μm² by the length 100 μm as shown in FIG. 17, and the obtained value is considered as the thick and thin degree (Step S6 of FIG. 3). The thick and thin degree corresponds to a width of a rectangle having the same area and the length of 100 μm, and can provide a practical image of the graphite structure.

Then the width 10.06 of the assumptive graphite piece is rounded to be 10.1, and visually shown with the number 90 of the detected graphite pieces as 90 (10.1) in form of "the number of the detected graphite pieces (the thick and thin degree)" (Step S7 of FIG. 3). The form of the graphite structure is indicated with the thick and thin degree of the graphite components. It should be noted that a series of the above arithmetic processing may be carried out in the image analysis apparatus 20 shown in FIG. 2.

Next, a conventional graphite spheroidizing ratio measuring apparatus is used to verify appropriateness and reasonableness of the method of evaluating the graphite structure of the gray cast iron comprising the thick and thin degree evaluation using a 2- or 3-digit value.

Figure 4:
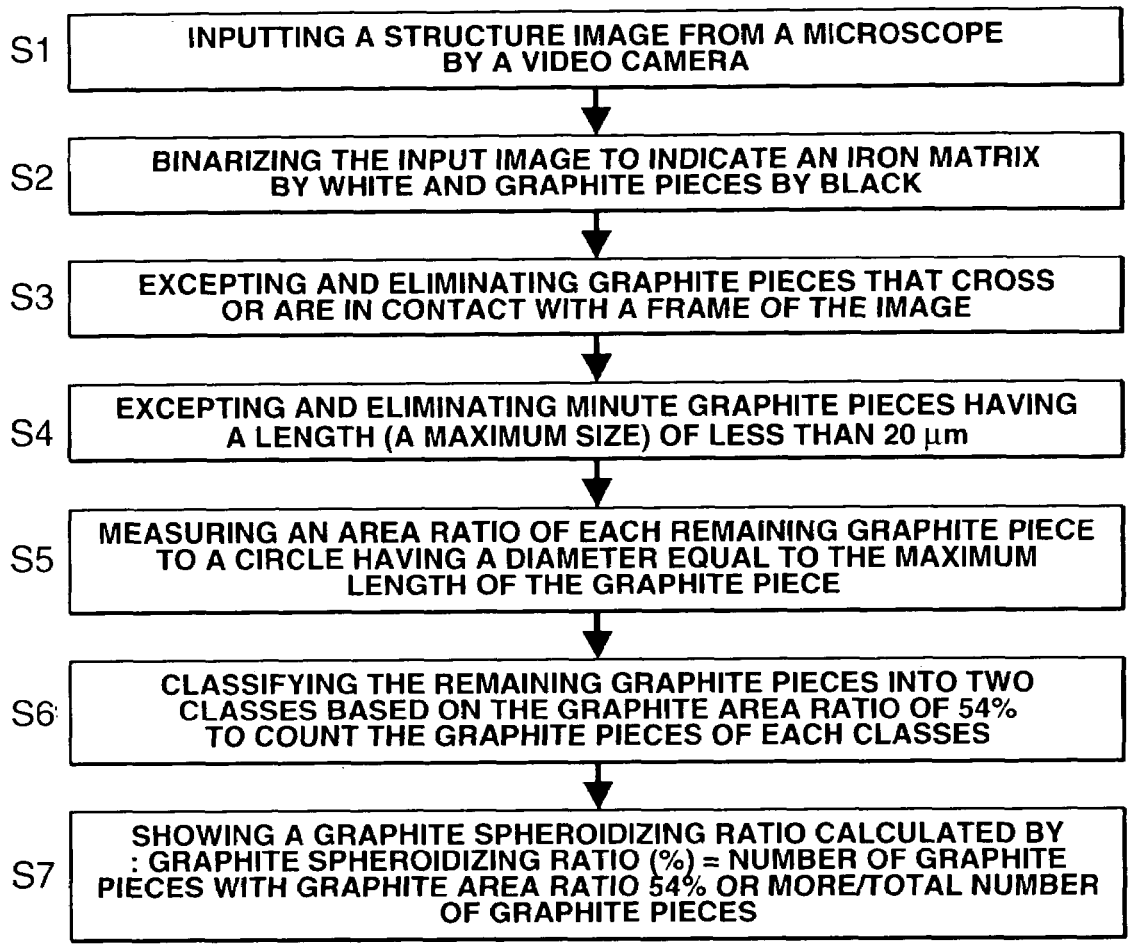
FIG. 4 is a flowchart showing steps of an image analysis for measuring a graphite spheroidizing ratio.

FIG. 4 shows steps of a measurement using a widely known graphite spheroidizing ratio measuring apparatus. As shown in FIG. 4, in the graphite spheroidizing ratio measurement, all the graphite pieces in the input image are distinguished based on a predetermined size and counted regardless of whether graphite pieces are spherical or non-spherical. A structure of flake-like or eutectic graphite pieces was quantitatively evaluated by utilizing this counting function.

For example, the 640×480 pixels (picture elements) of the 100 times magnified microscopic image input by the video camera 8 (the image pickup device such as a CCD) of FIG. 1 is used as an object of image analysis. There is the relation of 1 pixel=1 μm as describe above. An example of the analysis results is shown in FIG. 5, the numbers of the detected graphite pieces of different spherical or non-spherical (flake-like) shapes according to JIS being separately indicated.

As described above, the two methods of the maximum size method and the average size method can be used for determining the size of each graphite piece to be extracted. According to definition of JIS, the graphite spheroidizing ratio measurement is carried out by the maximum size method. However, the two methods are meaningful in some degree, whereby both of the maximum size method and the average size method are used in combination herein.

Figure 7:
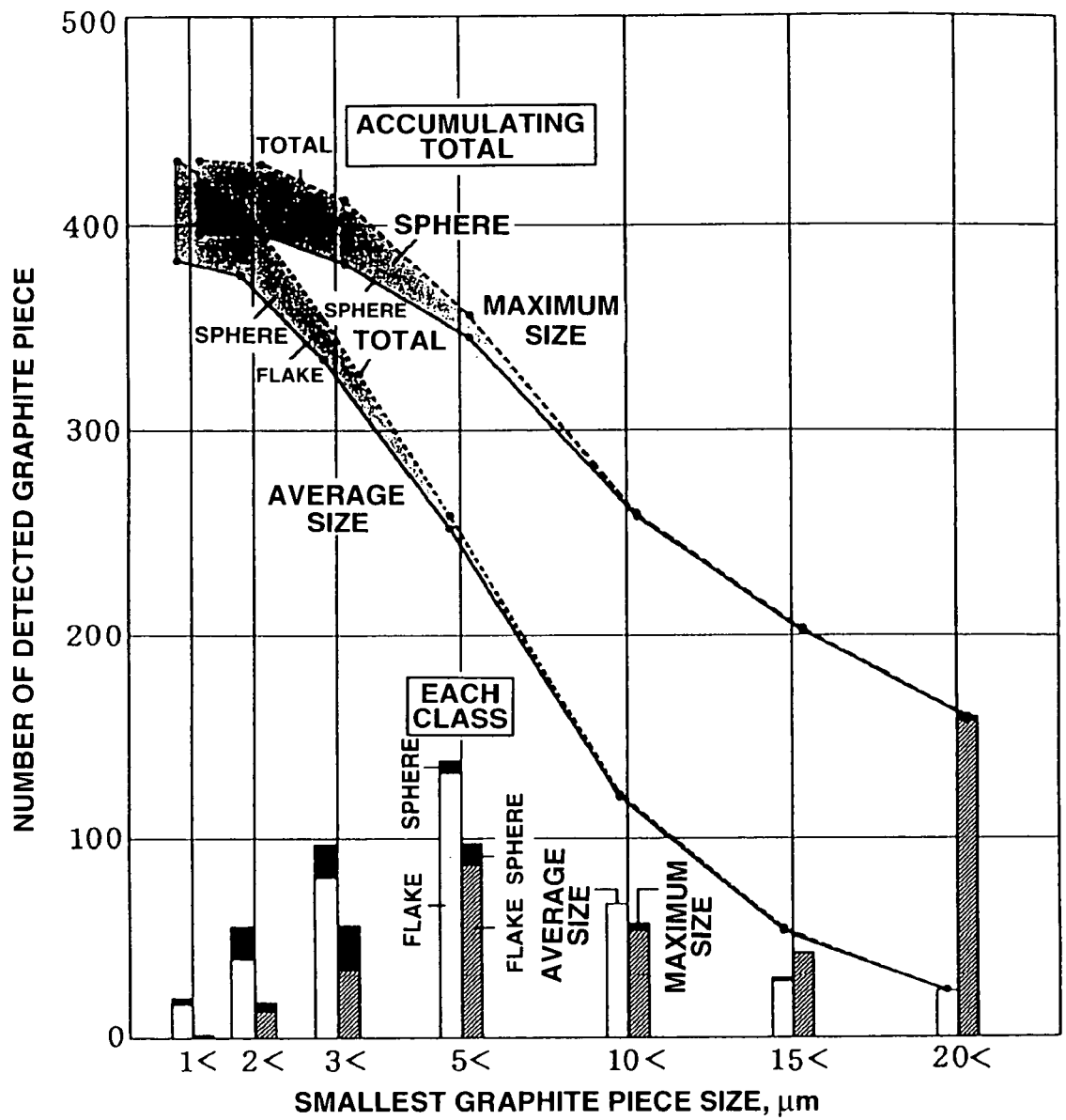
FIG. 7 is a graph showing numbers of detected graphite pieces of different shapes and sizes.

First three samples of a coarse graphite structure with relatively long graphite pieces, a minute eutectic graphite structure, and a middle thereof were prepared. FIG. 7 shows a result of evaluating the middle graphite structure to measure numbers of graphite pieces of different shapes and sizes as an example.

As shown in FIG. 7, the graphite pieces of several size classes were extracted. For example, the graphite pieces were classified into seven size classes of 1 μm or more, 2 μm or more, 3 μm or more, 5 μm or more, 10 μm or more, 15 μm or more, and 20 μm or more with respect to both of the maximum size and the average size. The results were shown as numbers of the detected graphite pieces of the size classes, accumulating total numbers, and numbers of the detected graphite pieces by the spherical or non-spherical shapes.

As shown in FIG. 7, the graphite piece number obtained by using the maximum size method was larger and the graphite piece number obtained by using the average size method was smaller in each relatively larger size class. On the other hand, in each smaller size class, the graphite piece number obtained by using the average size method was larger and the graphite piece number obtained by using the maximum size method was smaller. This is reasonable for the above-described definitions of the maximum size and the average size. In contrast, when the graphite pieces of the size class of 1 μm or more were counted, substantially all the graphite pieces in the image were detected regardless of the shape, and the total number of the graphite pieces measured by using the maximum size method was about 433, approximately the same as the number measured by using the average size method, about 436.

The results of measuring the other two samples of the coarse graphite structure and the eutectic graphite structure are not shown. In the case of the coarse graphite structure, the number of the detected graphite pieces of the size class of 1 μm or more was about 211 in the maximum size method and about 223 in the average size method. In the case of the eutectic graphite structure, the number of the detected graphite pieces of the size class of 1 μm or more was about 1172 in the maximum size method and about 1176 in the average size method. The results showed the same tendency as those of the middle graphite structure except for this difference.

Meanwhile, it was found that spherical graphite pieces were hardly observed in the size class of 5 or 10 μm or more and increased in the smaller size classes as a characteristic common in all the samples.

Figure 8:
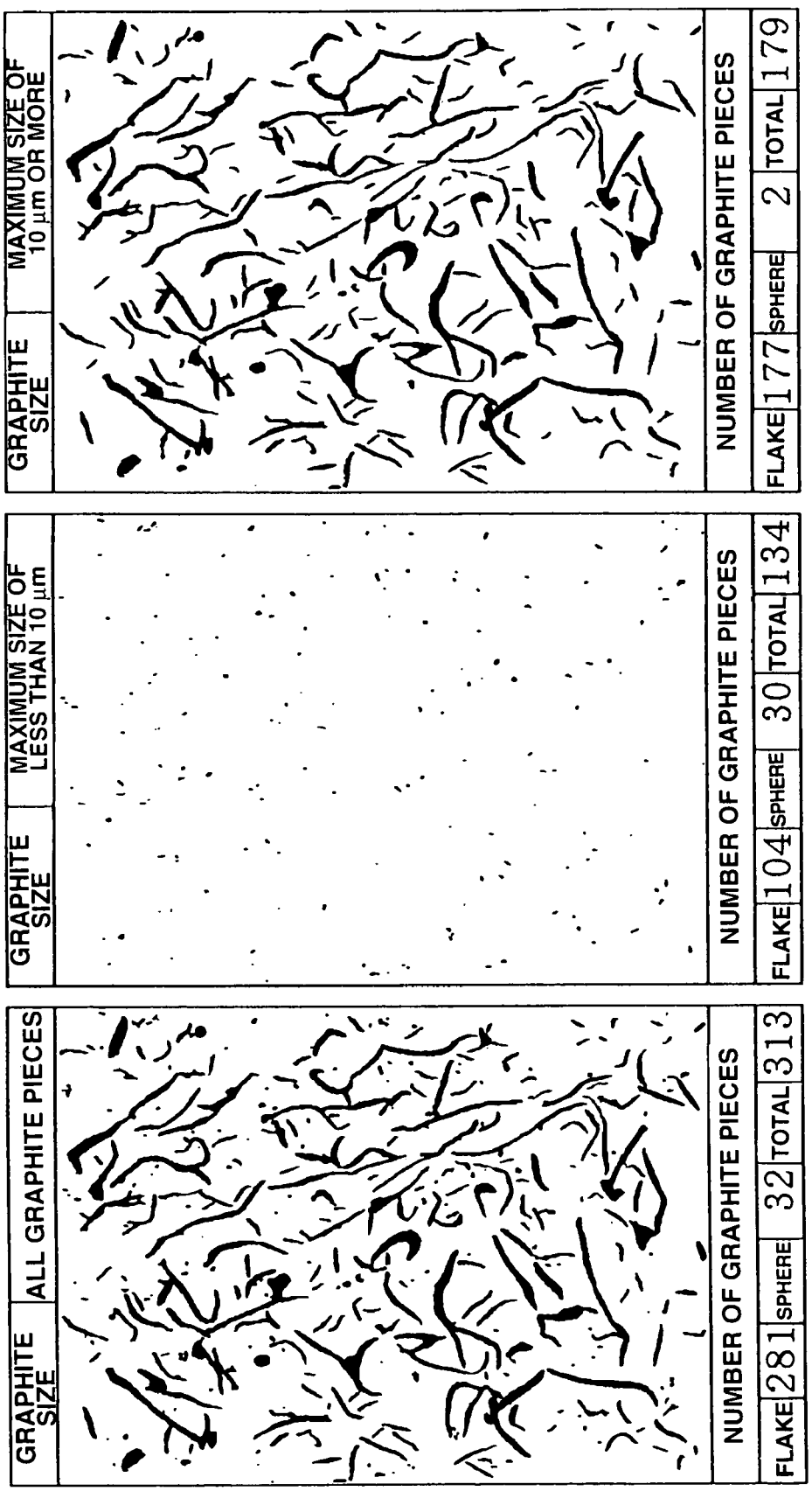
FIG. 8 is an explanatory view of dividing the graphite structure of the left into graphite pieces having a maximum size of less than 10 μm and graphite pieces having a maximum size of 10 μm or more.

Thus, graphite pieces of another sample was divided into maximum size classes of 10 μm or more and less than 10 μm or into average size classes of 5 μm or more and less than 5 μm, to observe differences between the divided graphite structures. FIG. 8 shows the result of dividing the graphite structure into the maximum size classes. In the maximum size class of less than 10 μm, the most of the detected 134 graphite pieces were point-like, granular, or nubbly, it was impossible to judge whether the pieces were spherical or non-spherical by visual observation, and there was a possibility that a part of the detected pieces was slag or rust in actuality. Further, it was important that, in visual observation, the impression or image of the graphite structure was formed by the graphite pieces with the maximum size of 10 μm or more, and the graphite pieces with the maximum size of less than 10 μm were considered as noise not to affect the impression. The same observation results were obtained also in the case where the graphite pieces were divided into the average size classes of 5 μm or more and less than 5 μm though not shown.

An object of the invention is to differentiate graphite structures, thereby clarifying differences between the structures. In view of the object, the point-like or granular graphite pieces having the maximum size of less than 10 μm or the average size of less than 5 μm do not affect the impression of the entire structure, to be nothing but noise. Therefore, the following observations cover only the non-spherical graphite pieces with the maximum size of 10 μm or more or the average size of 5 μm or more.

Conditions for measuring the numbers of the graphite pieces in the graphite structure were refined in the above manner, and then an experiment was performed under the refined conditions.

First, samples with various graphite structures were prepared, and ten samples of Nos. 1 to 10 were selected therefrom in the order from a longer graphite piece structure to a minute eutectic graphite piece structure such that approval was obtained from every one of 5 observers. Then, the graphite pieces were classified into 4 size classes of 5 μm or more, 10 μm or more, 15 μm or more, and 20 μm or more with respect to the maximum size method and the average size method, and the numbers of the non-spherical graphite pieces according to JIS were measured.

Figure 9:
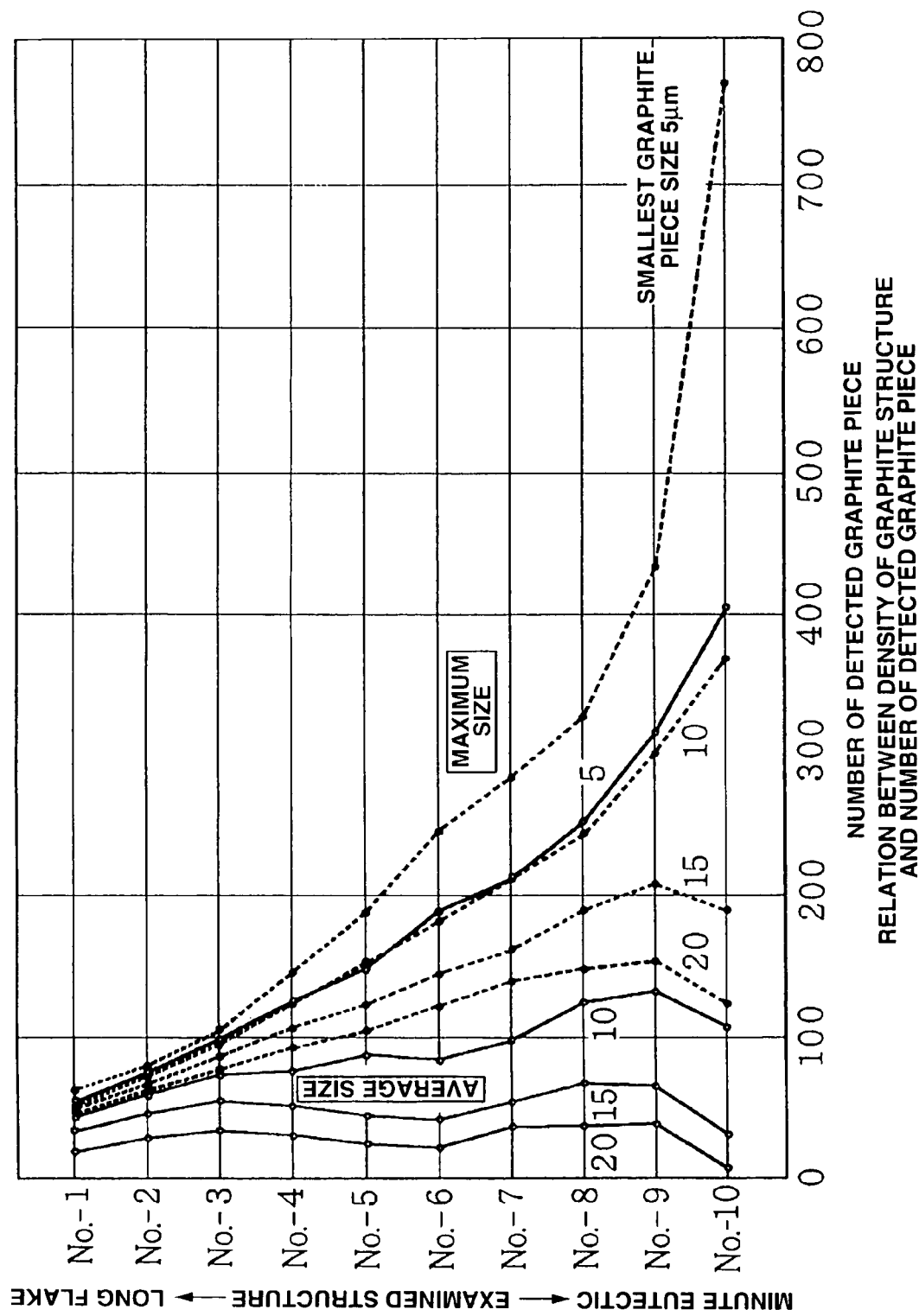
FIG. 9 is a graph showing a relation between a density of a graphite structure and a number of detected graphite pieces.

The results are shown in FIG. 9. The relations between the graphite structure states and the numbers of the detected graphite pieces are shown in the order of the structure densities from the longer flake graphite structures to the minute eutectic graphite structures. Data obtained by the maximum size method (dashed lines) and data obtained by the average size method (solid lines) are overlapped. It is clear from the results that the number of the graphite pieces with the average size of 5 μm or more and the number of the graphite pieces with the maximum size of 10 μm or more have the most linear relationship with the densities of the graphite structures. More samples were measured with respect to the numbers of the graphite pieces with the average size of 5 μm or more and the number of the graphite pieces with the maximum size of 10 μm or more, to judge which was the most effective method as a standard. The results are shown in FIG. 10.

Figure 10:
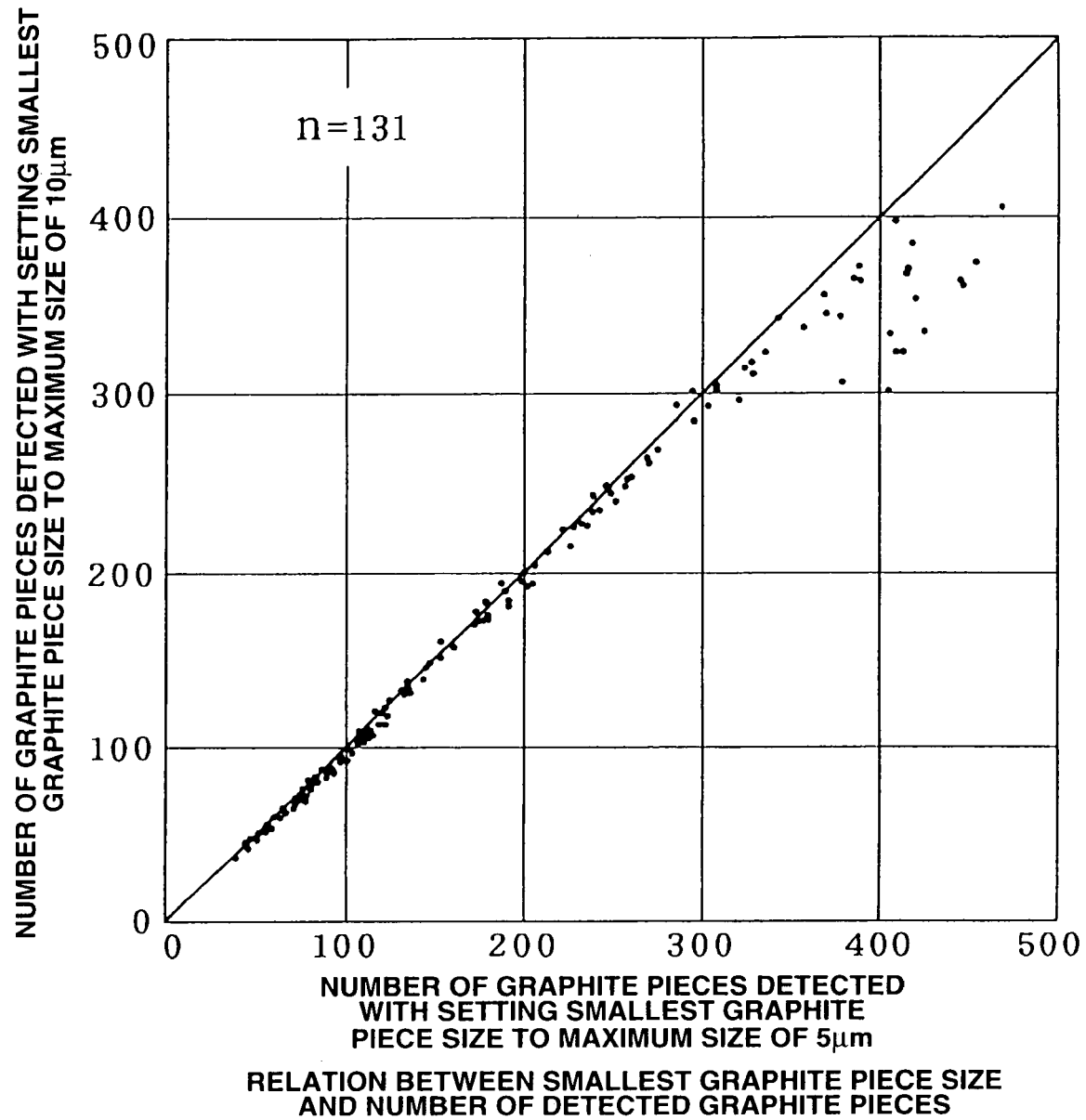
FIG. 10 is a graph showing a relation between a smallest graphite piece size and a number of detected graphite pieces.

As is clear from FIG. 10, though equal graphite piece numbers are obtained by both the size methods in the large graphite piece structures with a graphite piece number of approximately 300 or less, more graphite pieces are detected by using the average size of 5 μm or more in the relatively minute, nearly eutectic graphite structures with a graphite piece number of more than 300. The reason of this seems that, as described above, the lengths of the graphite pieces are used in the maximum size method and the areas of the graphite pieces are used in the average size method as a measure of the size. Thus, some of the nubbly, granular, or nearly point-like graphite pieces, which have a length smaller than the predetermined maximum size to be removed from the measurement (or detection or extraction) in the maximum size method, have an area more than the predetermined average size.

In the differentiation of the graphite structures, minuter graphite structures are more difficult to detect the differences therebetween than structures of relatively larger graphite pieces. It is remarkably preferred that the numbers of the graphite pieces are more precisely obtained even in the case of such minuter graphite structures, and as the conclusion, it is reasonable that the size of the smallest graphite piece to be extracted is determined using not the maximum size method but the average size method to evaluate the graphite structure based on the number of the graphite components.

It is clear from the above study results that, by measuring the number of the non-spherical (flake-like) graphite pieces with the average size of 5 µm or more, the graphite structure of the gray cast iron can be reliably evaluated with ease without differences between individuals while calculating the 2- or 3-digit thick and thin degree value as described above.

Figure 11:
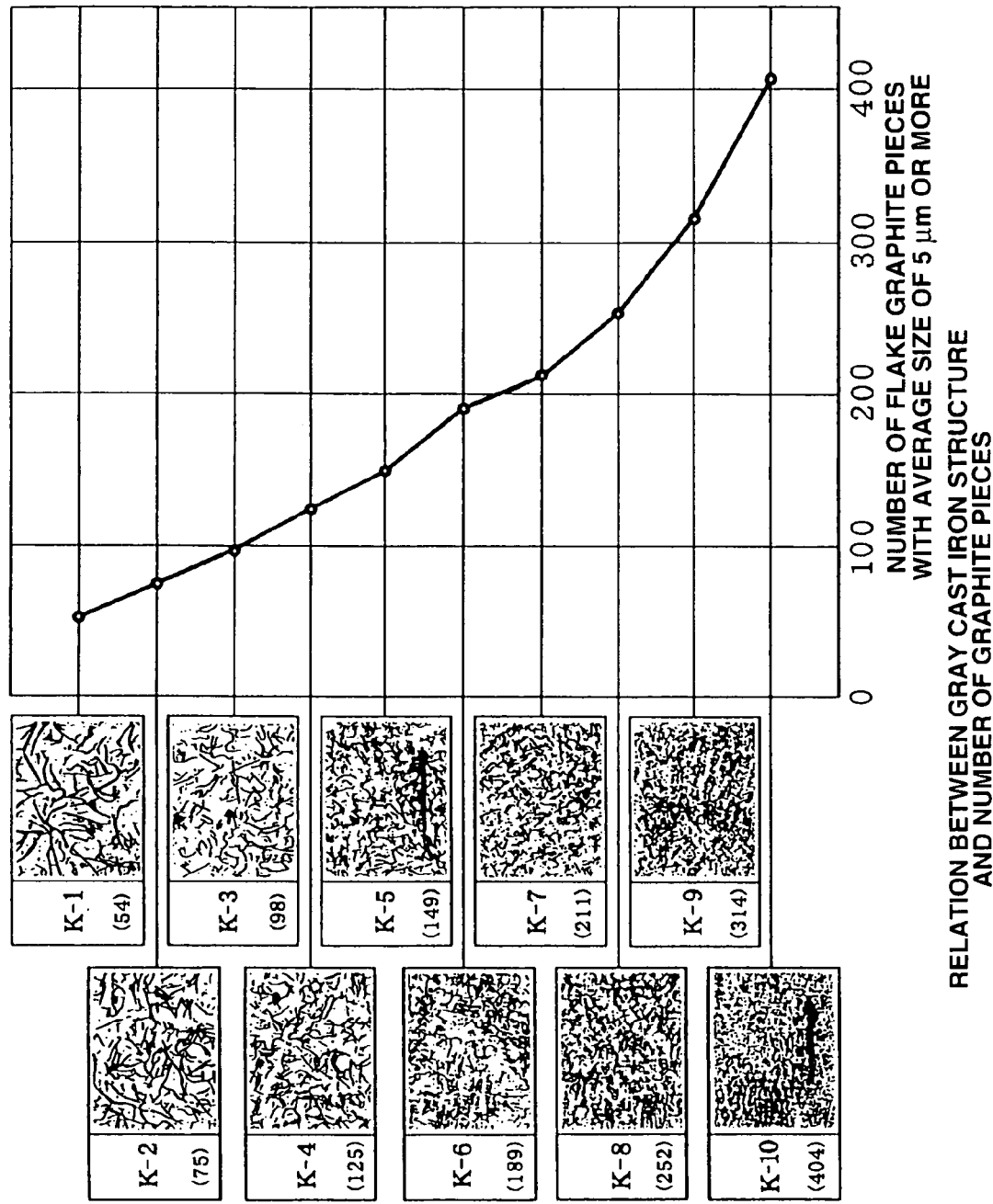
FIG. 11 is an explanatory view showing a relation between a gray cast iron structure and a number of graphite pieces.

FIG. 11 shows a relation between the micrographs and the numbers of the detected flake graphite pieces of the above ten samples of Nos. 1 to 10 as a further example. It is clear that the form of the graphite pieces in each structure has a certain correlation with the number of the detected graphite pieces. In FIG. 11, the samples of Nos. 1 to 10 are shown as K-1 to K-10, and the numbers of the detected non-spherical (flake-like) graphite pieces are shown in parentheses.

There is a case where graphite structures having the same detected graphite piece numbers are different in thickness of the component graphite pieces, and herein influences of these differences are not necessarily taken into account sufficiently. A degree of the thickness (or the thinness) of the graphite pieces is temporarily referred to as a thick and thin degree, and an example of graphite structures with remarkably different thick and thin degrees are shown in FIG. 12.

Figure 12:
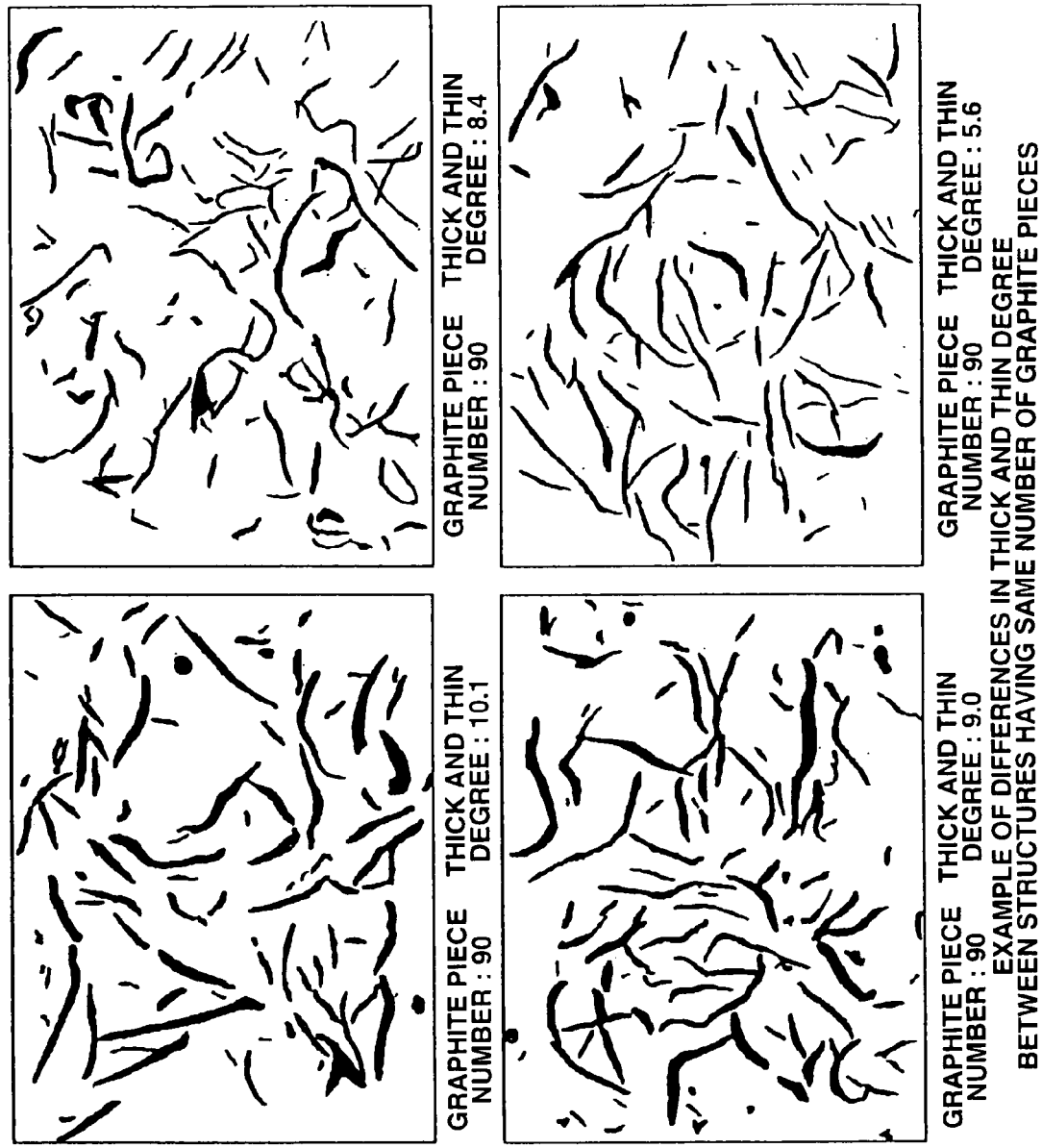
FIG. 12 is an explanatory view showing an example of differences in thick and thin degree between structures having the same number of graphite pieces.

The graphite structures shown in FIG. 12 are different in the thick and thin degrees of the graphite pieces as is clear from the graphite area ratios though they has the same detected graphite piece number of 90. The gray cast irons having the different structures are naturally different in mechanical properties, etc. Thus, it must be said that the method of evaluating the graphite structure is not perfect without taking the thick and thin degree into account.

In this case, the simplest is a method comprising comparing the total graphite areas of the structures having the same graphite piece numbers, or a method comprising comparing average areas of the graphite pieces, which are each obtained by dividing the total graphite area by the graphite piece number, and the methods are effective to some extent. However, the structures have different size distributions of the graphite pieces though they have the same graphite piece numbers, whereby the methods of simply comparing the areas of the graphite pieces are not always appropriate.

Figure 13:
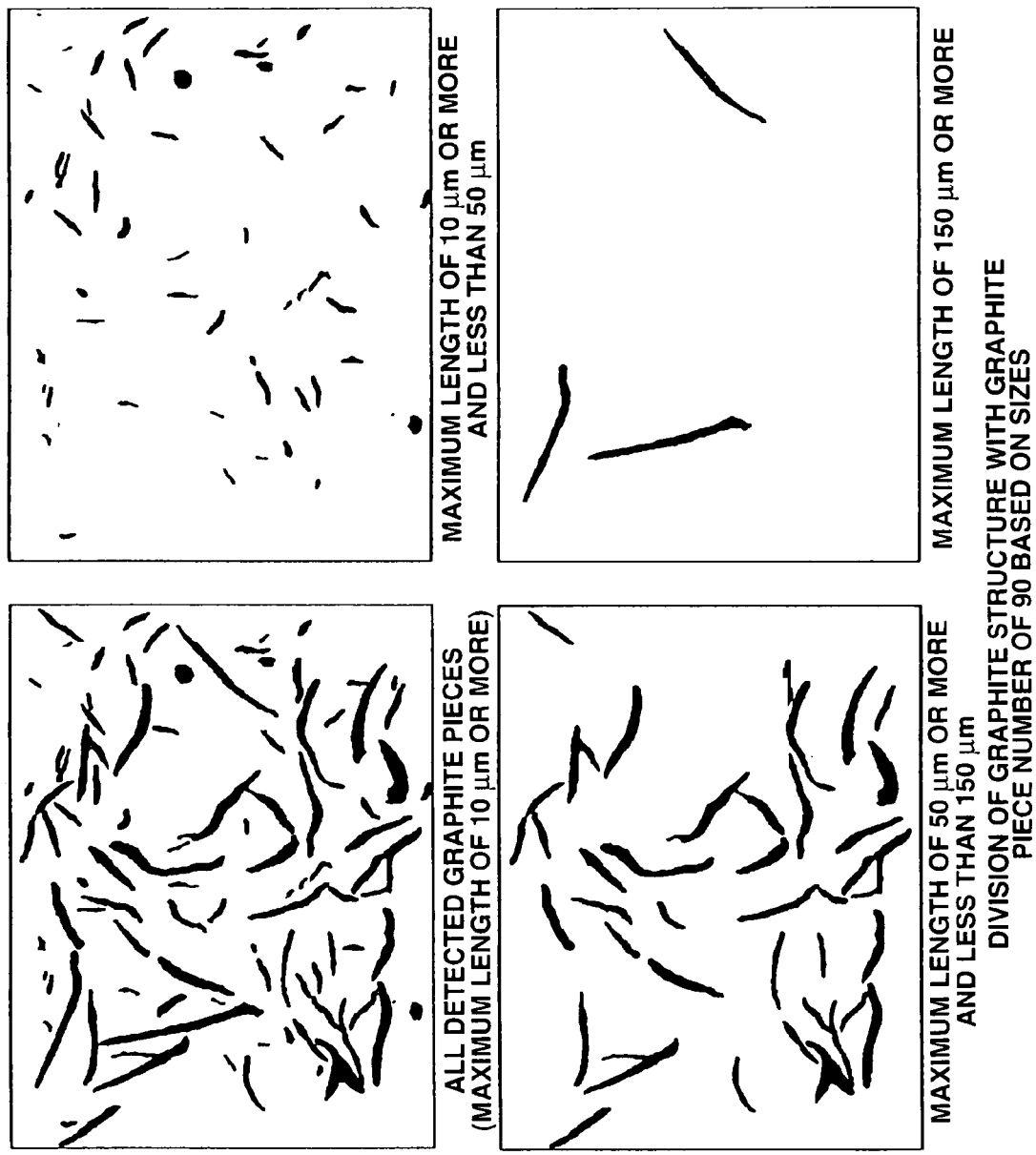
FIG. 13 is an explanatory view of dividing the graphite structure with a graphite piece number of 90 based on the sizes.

Thus, among 4 types of the graphite structures shown in FIG. 12, the structure having the thick and thin degree of 10.1 shown in the upper left is divided by distributing the graphite pieces into 3 maximum size classes of 10 µm or more and less than 50 µm, 50 µm or more and less than 150 µm, and 150 µm or more, and shown in FIG. 13. The upper left of FIG. 13 is the same as that of FIG. 12. As is clear from FIGS. 12 and 13, the impression of swelling of the graphite pieces in the graphite structure mainly depends on the graphite pieces having a maximum length of 50 µm or more and less than 150 µm. Another graphite structure having a different graphite piece number was checked in the same manner for an experiment, and as a result, the graphite pieces with a maximum length of 50 µm or more and less than 150 µm significantly affected the impression of swelling. Therefore, the impression of swelling of the graphite pieces in the entire graphite structure can be shown as the thick and thin degree of the graphite pieces with the maximum length of 50 µm or more and less than 150 µm.

Figure 14:
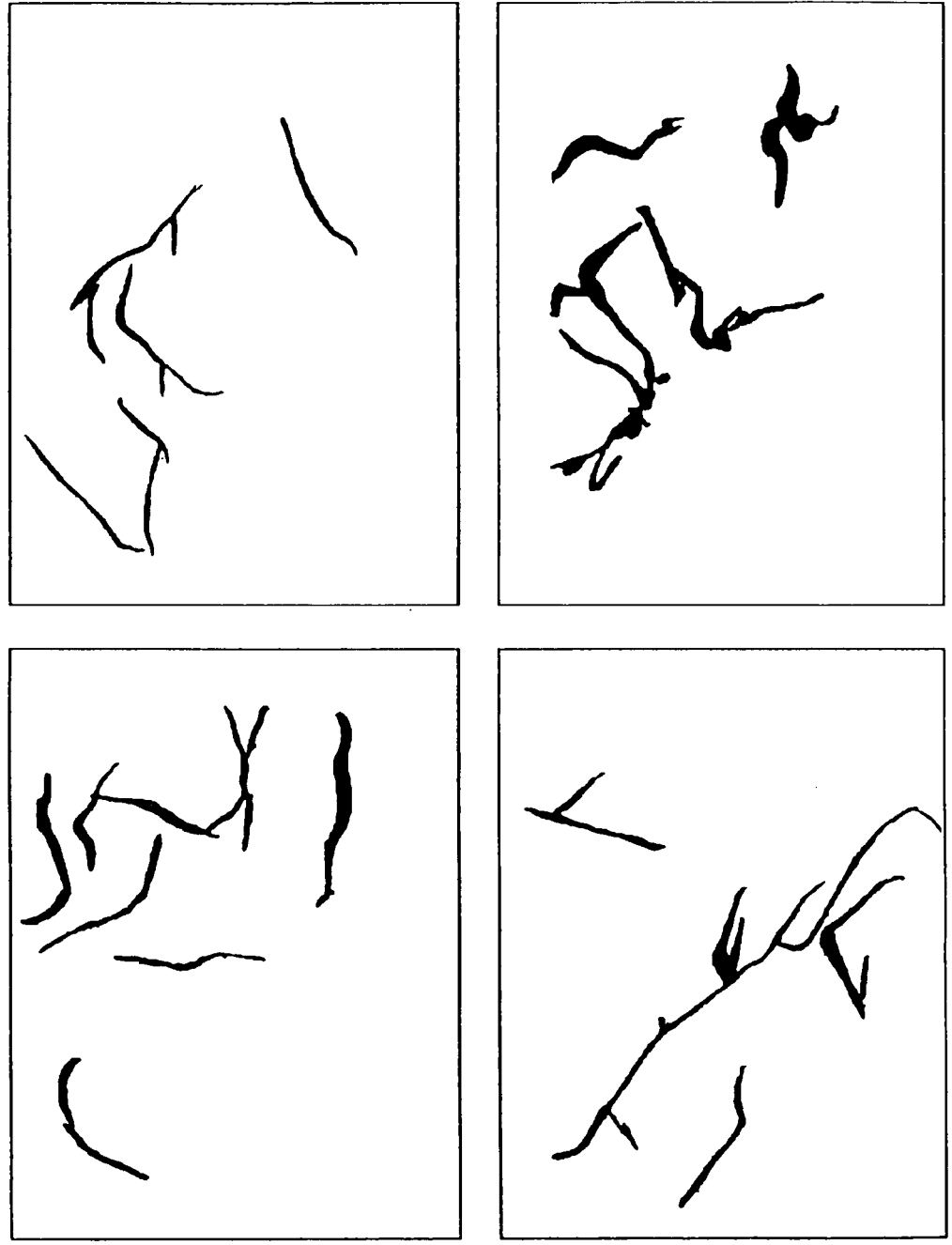
FIG. 14 is an explanatory view of linkage of a plurality of graphite pieces, which is increased among graphite pieces with a size of approximately 150 μm or more.

A plurality of graphite pieces may be linked and recognized as one graphite piece, and the linkage is remarkably increased among the graphite pieces having the maximum length of 150 µm or more as shown in FIG. 14. The graphite pieces having the maximum length of 150 µm or more are desirably excepted to prevent the miss-recognition.

Figure 15:
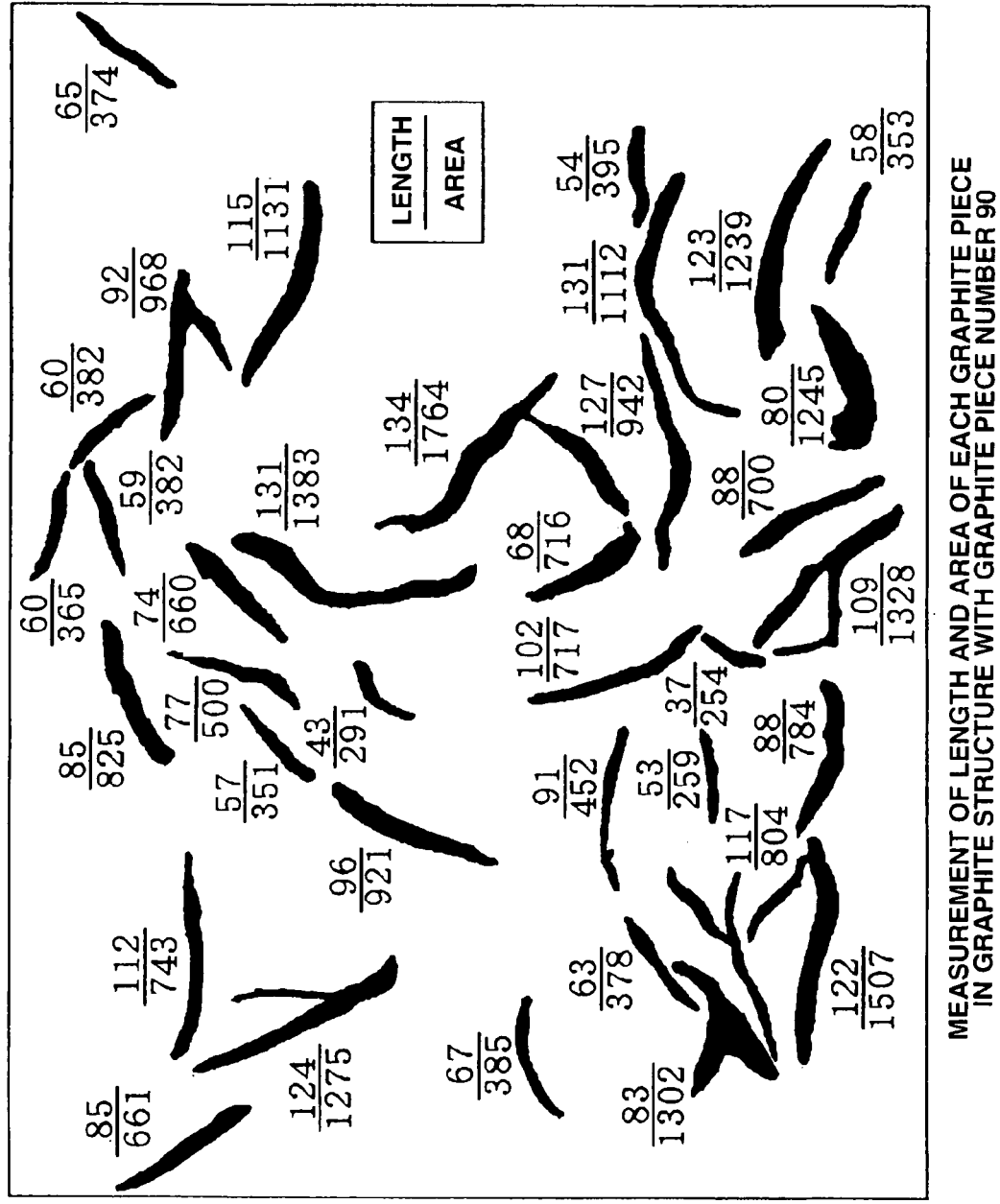
FIG. 15 is an explanatory view showing a result of measuring a length and an area of each graphite piece in the graphite structure with the graphite piece number of 90.

The maximum sizes (the maximum lengths) and the areas of the above graphite pieces of 50 µm or more and less than 150 µm are measured and shown together in FIG. 15, and the distribution of the graphite pieces is shown as a graph in FIG. 16. An area 1006 µm² of a graphite piece having the median 100 µm of the lengths can be obtained from FIGS. 15 and 16.

The assumptive graphite piece with the maximum length (the maximum size) of 100 µm, which may be representative of the graphite pieces, is obtained from the data of the graphite pieces of 50 µm or more and less than 150 µm, the area of the assumptive graphite piece is calculated to be 1006 µm², and a value 10.06 is obtained by dividing the area 1006 µm² by the length 100 µm as shown in FIG. 17. The value corresponds to the width of the rectangle having the same area and the length of 100 µm, and can provide a practical image of swelling.

Then, the width 10.06 of the assumptive graphite piece is rounded to be 10.1, and shown with the number 90 of the detected graphite pieces as 90 (10.1), whereby the thick and thin degree of the graphite components is indicated with the form of the graphite structure.

As described above, it is confirmed that the thick and thin degree evaluation using a 2- or 3-digit value is appropriate.

Figure 18:
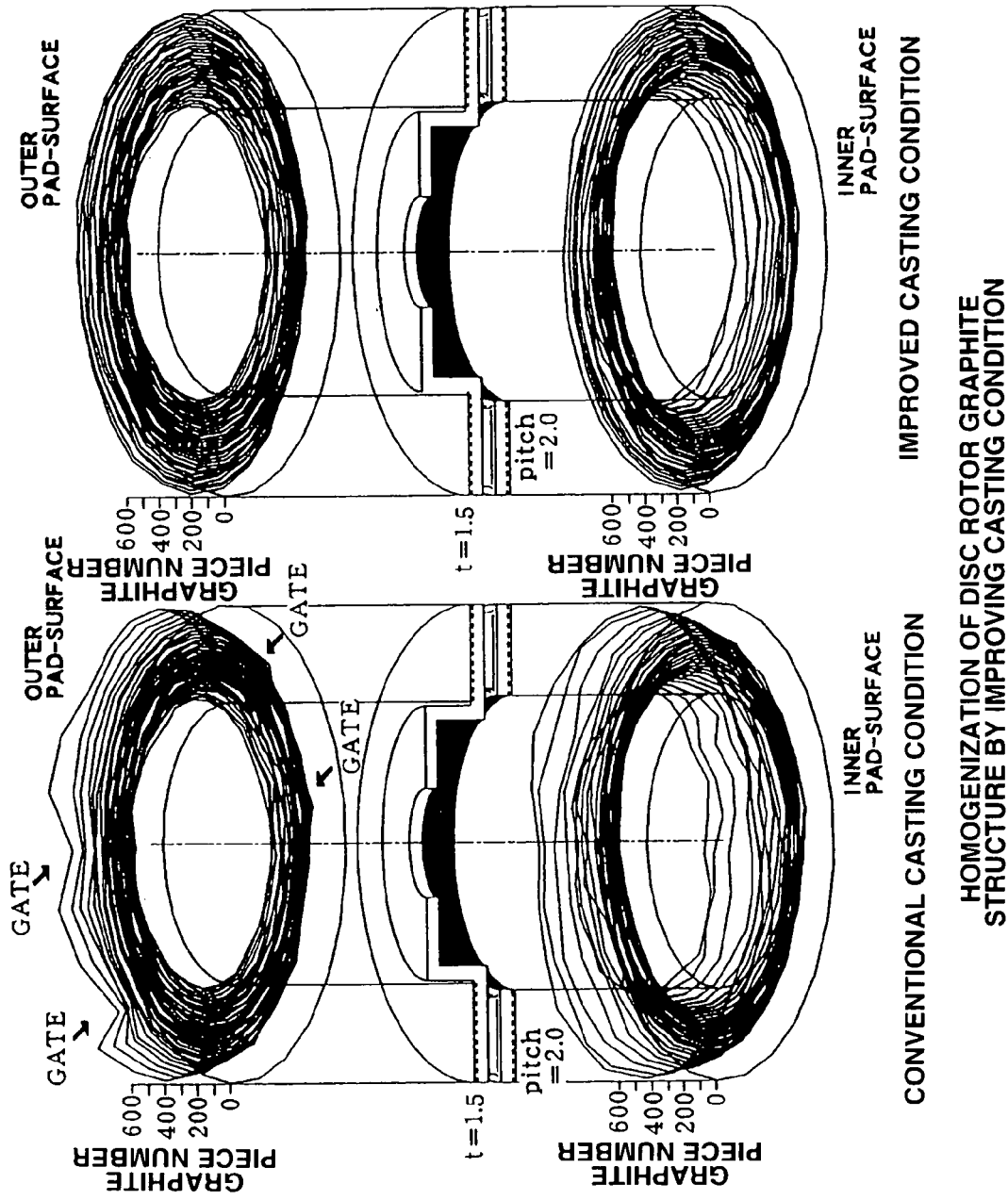
FIG. 18 is an explanatory view showing distribution of graphite pieces in sections of a brake disc rotor made of a cast iron three-dimensionally to improve a condition of casting the brake disc rotor.
Figure 19:
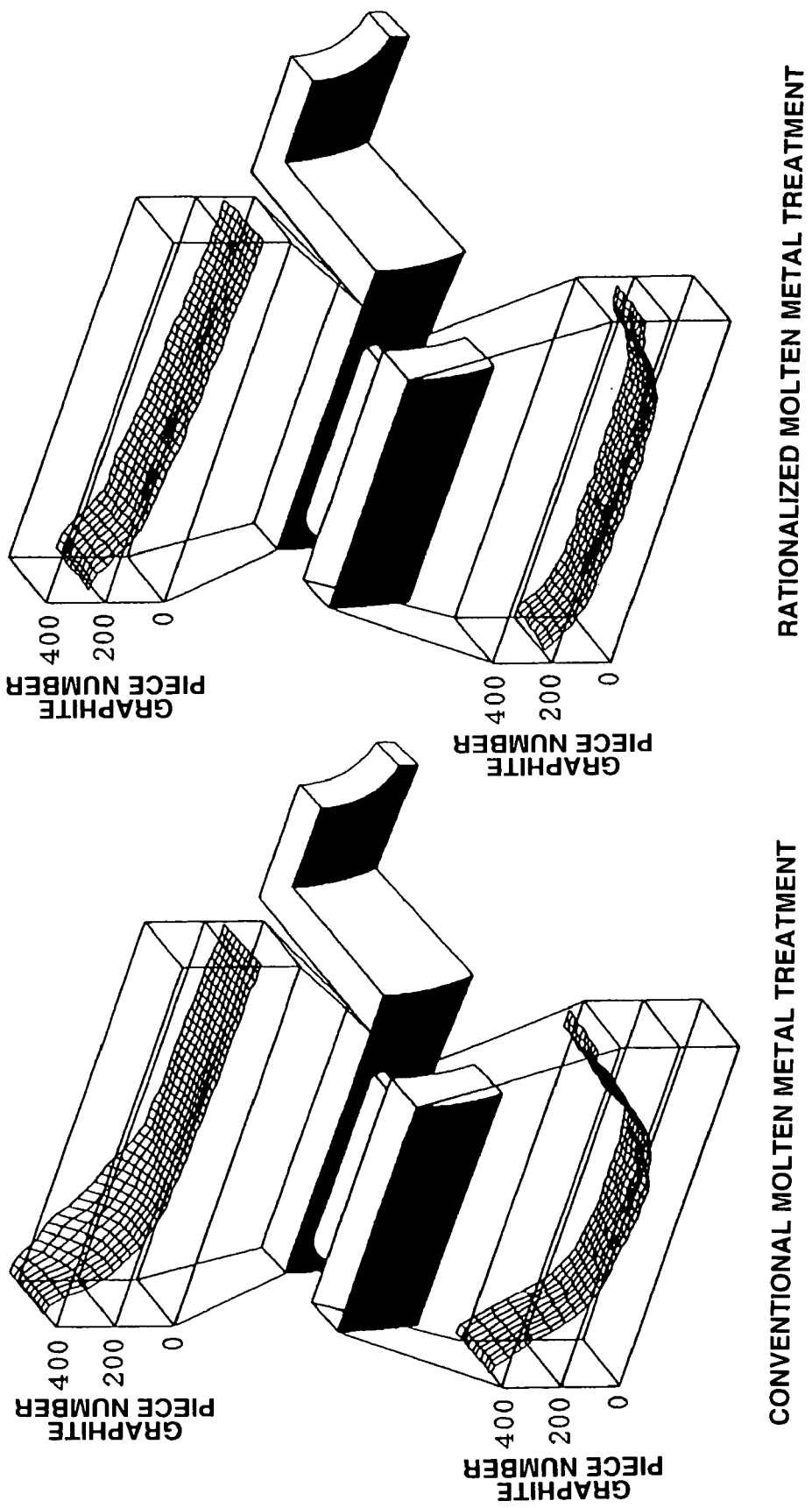
FIG. 19 is an explanatory view showing distribution of graphite pieces in sections of the brake disc rotor three-dimensionally to rationalize a molten metal treatment.

In production of a brake disc rotor made of a cast iron, distribution of graphite pieces in sections of the brake disc rotor is three-dimensionally shown to improve the casting condition in FIG. 18, and distribution of graphite pieces in sections of the brake disc rotor is three-dimensionally shown to rationalize the molten metal treatment in FIG. 19. It is more effective that the numeric values of the graphite structure are shown together with the above-described thick and thin degrees.

FIGS. 20 to 24 show a second embodiment of the invention.

Figure 20:
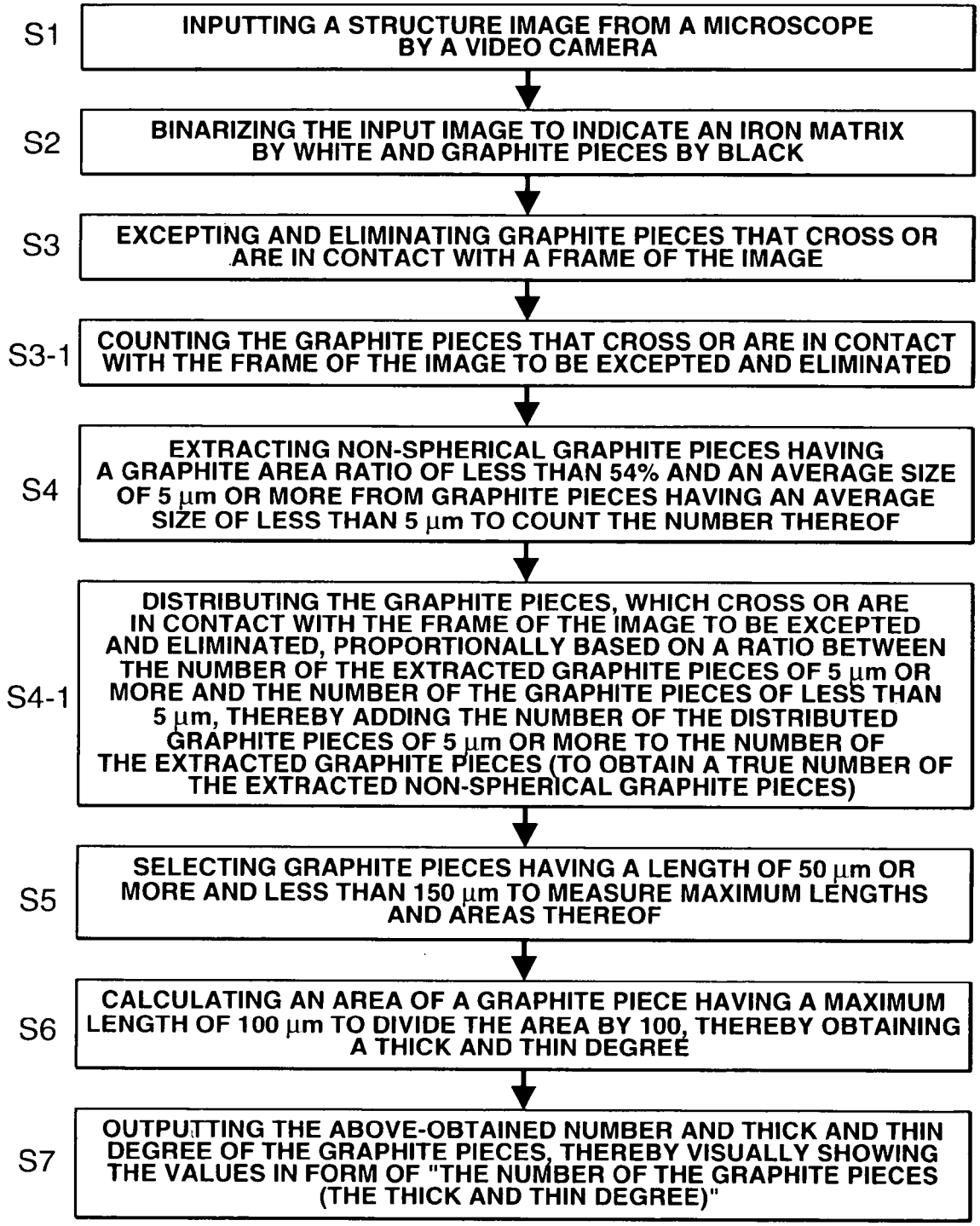
FIG. 20 is a flowchart showing a second embodiment of the invention.

As shown in the flowchart of FIG. 20, the graphite pieces, which cross or are in contact with the frame of the magnified image for the image analysis, are not measuring objects to be excepted and eliminated in the preprocessing step regardless of whether the graphite pieces are spherical or non-spherical (See, Step S3 of FIGS. 3 and 20). The graphite pieces in contact with the frame are excepted and eliminated because they cannot be examined with respect to shape and size of the unshown portions other than the portions shown in the image, and this procedure is unavoidable for the image analysis.

In the measurement of the graphite spheroidizing ratio, even if the number of the extracted graphite pieces for the measurement is slightly less than the actual number thereof, the graphite spheroidizing ratio can be obtained by measuring the graphite pieces remaining in the frame without serious practical problems.

On the other hand, in the invention, the flake graphite structure of the gray cast iron is quantitatively evaluated based on a graphite component piece number, whereby it is never preferred from the viewpoint of the evaluation accuracy that the important graphite piece number is different from the actual one.

Figure 21:
FIG. 21 is an explanatory view of comparing graphite structures observed before and after excepting and eliminating graphite pieces in contact with a frame of an image for analysis.

FIG. 21 shows a comparison of structures observed before and after excepting and eliminating graphite pieces which cross or are in contact with a frame of an image (a measurement frame). When the graphite pieces in contact with the frame are excepted and eliminated, there are conspicuous empty spaces in the vicinity of the frame, as shown in the right of FIG. 21. Only the graphite pieces remaining within the frame are used as the measurement objects, and as a result, the analyzed graphite structure is partly different from the actual structure though the structures are similar.

The gray cast iron has a content of the thin long graphite pieces much higher than that of a spherical graphite cast iron containing spherical or nubbly graphite pieces. The longer flake graphite pieces are more likely to come into contact with the image frame. Further, the graphite piece number becomes smaller as the graphite pieces are longer, and thus the graphite structure containing the longer graphite pieces has a higher ratio of the excepted and eliminated graphite pieces in contact with the frame.

Figure 22:
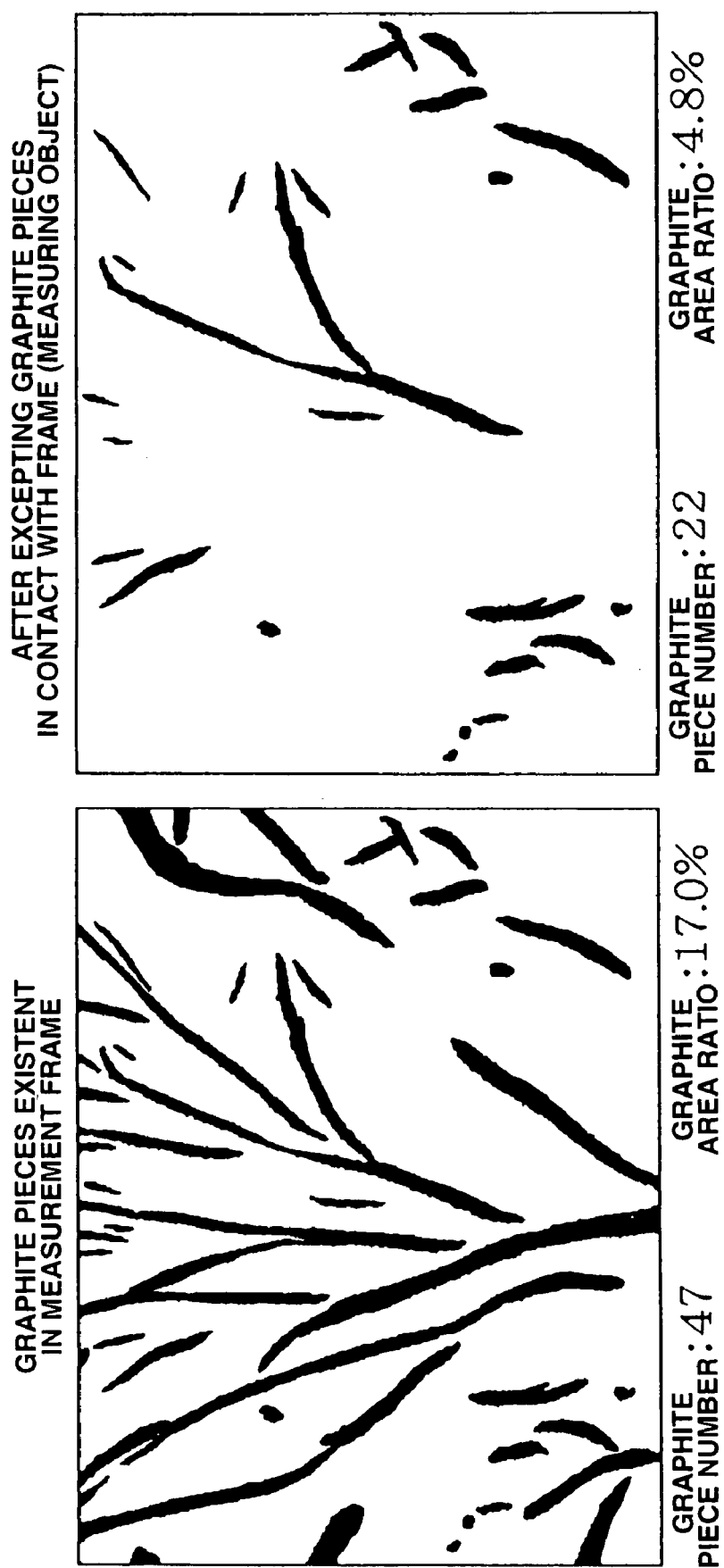
FIG. 22 is an explanatory view also of comparing graphite structures observed before and after excepting and eliminating graphite pieces in contact with a frame of an image for analysis.

A specific conspicuous example is shown in FIG. 22, and the measuring object graphite structure is made very different from the original by excepting and eliminating more than half of the present graphite pieces as shown in the right of the FIG. 22. A structure of extremely long graphite pieces is used in this example, and such a large difference is not observed in common FC-250 graphite structures. However, in the case of evaluating common, so-called A-type graphite structures by using an image of 640×480 µm, approximately 5 to 20% of the graphite pieces are in contact with the frame to be excepted and eliminated unavoidably.

Because graphite structures containing similar graphite pieces show similar ratios of the excepted and eliminated graphite pieces, relative comparison of the structures can be carried out without serious practical problems. However, to faithfully reflect the original graphite structure to the evaluation, it is preferable to evaluate also the excepted and eliminated graphite pieces.

Though it is impossible to measure the shapes and the sizes of the graphite pieces in contact with the frame to be excepted and eliminated as described above, the number thereof can be measured. Further, it is believed that the graphite pieces in contact with the frame have the shapes and the sizes not so different from those of the most graphite pieces remaining in the frame stochastically.

Thus, a graphite structure extremely similar to the original structure with the entire graphite pieces can be reproduced while taking account of the number of the graphite pieces in contact with the frame to be excepted and eliminated by the steps of counting the graphite pieces in contact with the frame to be excepted and eliminated; classifying the graphite pieces remaining in the frame into a plurality of size classes to count the number of the graphite pieces of each size class; calculating the distribution ratio between the numbers of the remaining graphite pieces of the size classes; and distributing the graphite pieces to be excepted and eliminated into the size classes proportionally based on the ratio, to add a number of the distributed graphite pieces to the above numbers.

Figure 23:
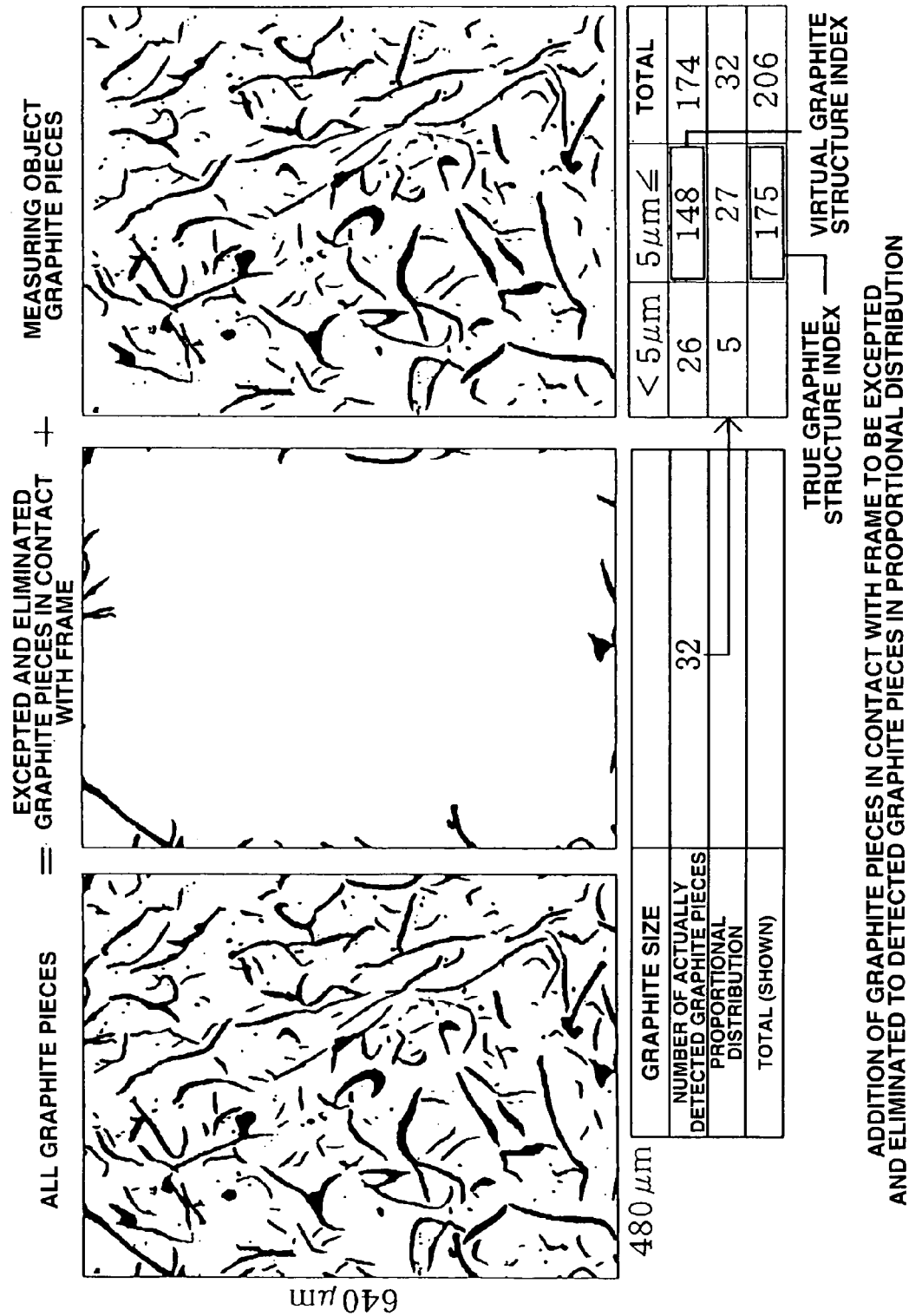
FIG. 23 is an explanatory view of adding a number of graphite pieces in contact with an image frame to be excepted and eliminated in a proportional distribution.
Figure 24:
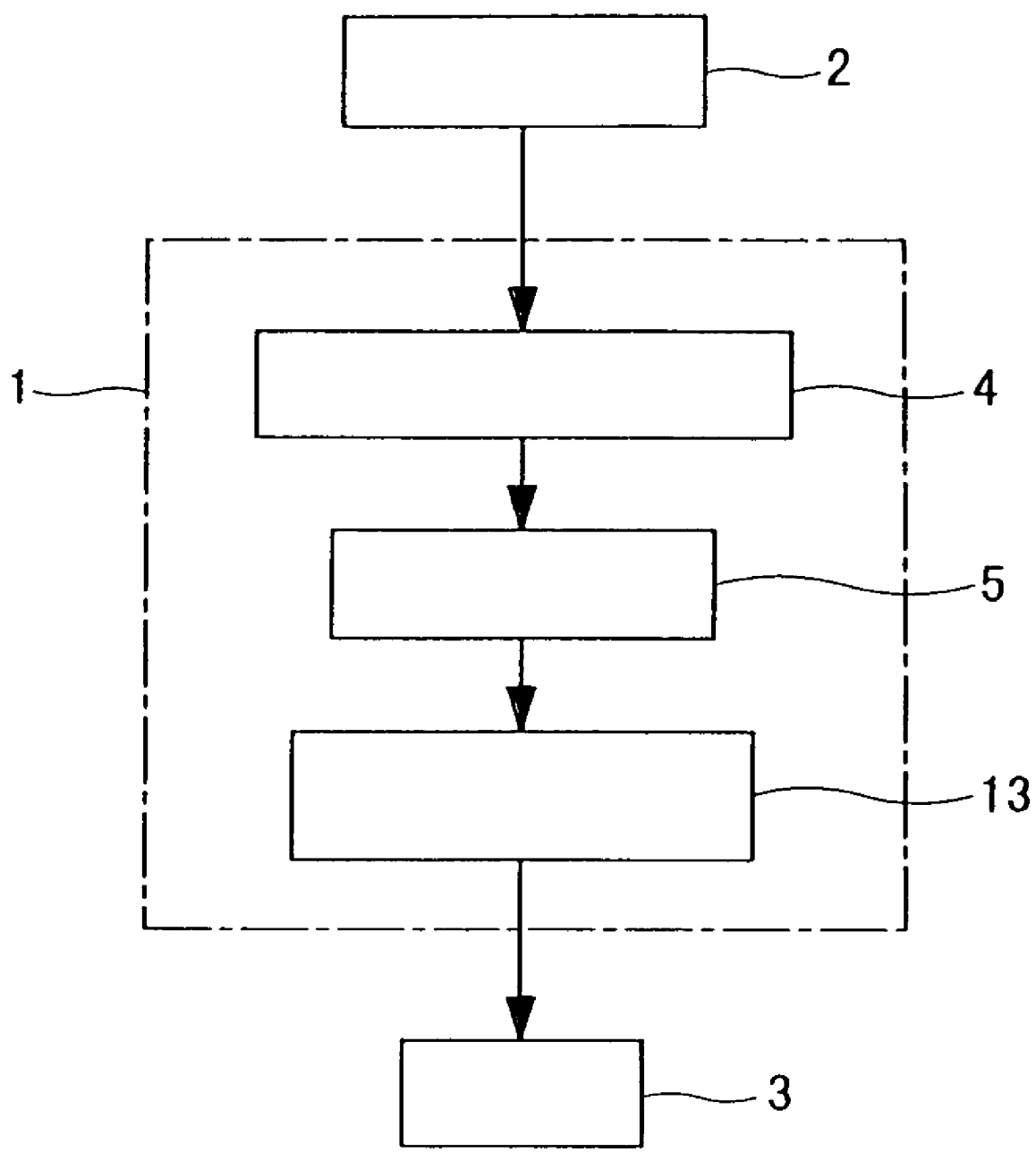
FIG. 24 is a functional block diagram showing a modified example of FIG. 2.

FIG. 23 shows a specific example of the steps of FIG. 20, and Steps S1 to S3 of FIG. 20 are equal to those of FIG. 3. When the graphite pieces, which cross or are in contact with the frame of the image binarized into bright and dark, are excepted and eliminated from the image of the graphite structure (the entire graphite pieces) in Step S3, the number of the graphite pieces to be excepted and eliminated is counted (Step S3-1). Then, as the case of FIG. 3, the non-spherical graphite pieces having the graphite area ratio of less than 54% and the average size of 5 µm or more are extracted and separated from the graphite pieces of less than 5 µm, and the numbers of the classified non-spherical graphite pieces are counted or calculated in Step S4.

In the example of FIG. 23, the number of the graphite pieces, which cross or are in contact with the frame of the image to be excepted and eliminated, is 32, the number of the graphite pieces of less than 5 µm in the frame is 26, and the number of the graphite pieces of 5 µm or more is 148.

Next, as shown in FIG. 23 in addition to Step S4-1 of FIG. 20, the 32 graphite pieces to be excepted and eliminated are classified based on the ratio of the number 26 of the graphite pieces of less than 5 µm and the number 148 of the graphite pieces of 5 µm or more remaining in the frame. Thus, the number 32 of the graphite pieces to be excepted and eliminated is divided into 5 and 27 proportionally based on the ratio of 26:148. The number 27 is added to the number 148 of the graphite pieces of 5 µm or more remaining in the frame, thereby correcting the number into 175. As a result, a virtual graphite structure index of 148, which does not depend on the number of the graphite pieces in contact with the frame to be excepted and eliminated, and a true graphite structure index of 175 approximate to the actual value, which is corrected by proportionally distributing the graphite pieces to be excepted and eliminated, are obtained as the numbers of the graphite pieces with the average size of 5 µm or more to be extracted.

Subsequently the thick and thin degree is calculated in Steps S5 and S6 and visually shown together with the above obtained true graphite structure index as 175 (10.1) in Step S7 as the case of FIG. 3. It should be noted that a series of the above arithmetic processing may be carried out in the image analysis apparatus shown in FIG. 24. The apparatus shown in FIG. 24 comprises a unit 13 for proportionally adding the number of the graphite pieces in contact with the image frame to be excepted, and is thereby different from the apparatus shown in FIG. 2.

In this embodiment, the number of the extracted non-spherical graphite pieces of the particular size class is corrected by proportionally distributing the graphite pieces, which cross or are in contact with the frame of the image to be excepted and eliminated, whereby the accuracy of the graphite structure image analysis can be further improved to provide the highly reliable evaluation results.

The invention claimed is:

1. A method for quantitatively evaluating a graphite structure of a gray cast iron by an image analysis apparatus, comprising the steps of using the image analysis apparatus to perform the steps of:

analyzing a magnified image of the graphite structure to extract non-spherical graphite pieces having sizes within a first range, contained in the graphite structure to calculate a number of the extracted non-spherical graphite pieces;

calculating a thick and thin degree expressing a representative degree of thickness of the non-spherical graphite pieces including measuring a maximum length and an area of each of the non-spherical graphite pieces having maximum lengths within a second range, included in the extracted non-spherical graphite pieces, determining an area of a non-spherical piece having a median value of the maximum lengths within the second range depending on the calculated maximum lengths and the areas, and dividing the determined area by the median value to obtain the thick and thin degree; and outputting the calculated number and the thick and thin degree of the non-spherical graphite pieces in combination as an evaluation result.

2. The method for evaluating a graphite structure of a gray cast iron according to claim 1, wherein the magnified image for the image analyzing step is taken from a microscopic screen image of the graphite structure by an image pickup device.

3. The method for evaluating a graphite structure of a gray cast iron according to claim 1, wherein the non-spherical graphite pieces are extracted to calculate the number thereof based on a diameter of a circle having an area equal to that of each graphite piece or on a maximum length of each graphite piece.

4. The method for evaluating a graphite structure of a gray cast iron according to claim 1, wherein the smallest graphite piece of the non-spherical graphite pieces extracted to calculate the number thereof has a size of an area equal to that of a circle having a diameter of 5 μm or a maximum length of 10 μm.

5. The method for evaluating a graphite structure of a gray cast iron according to claim 4, wherein the smallest graphite piece of the non-spherical graphite pieces extracted to calculate the number thereof has a size of an area equal to that of a circle having a diameter of 5 μm.

6. The method for evaluating a graphite structure of a gray cast iron according to claim 1, wherein the total area of the extracted non-spherical graphite pieces is divided by the total number thereof to obtain the thick and thin degree.

7. A computer-readable recording medium storing a program for carrying out the steps recited in claim 1.

8. A method for quantitatively evaluating a graphite structure of a gray cast iron by an image analysis apparatus, comprising the steps of using the image analysis apparatus to perform the steps of:

analyzing a magnified image of the graphite structure, thereby extracting non-spherical graphite pieces of a particular size class contained in the graphite structure to calculate the number and areas of the non-spherical graphite pieces;

calculating a thick and thin degree expressing a degree of thickness of the non-spherical graphite pieces based on the number and the areas; and outputting the number and the thick and thin degree of the non-spherical graphite pieces in combination as an evaluation result wherein the magnified image is preprocessed to except and eliminate graphite pieces in contact with a frame of the magnified image before extracting the non-spherical graphite pieces of the particular size class, and the number of the extracted non-spherical graphite pieces of a particular size class is corrected by the steps of counting the graphite pieces to be excepted and eliminated;

classifying graphite pieces other than the graphite pieces to be excepted and eliminated into a plurality of size classes containing the particular size class, to count a number of the other graphite pieces of each size class; and distributing the graphite pieces to be excepted and eliminated into the size classes proportionally based on a ratio between the numbers of the other graphite pieces, to add a number of the distributed graphite pieces to the numbers of the other graphite pieces.

9. A method for quantitatively evaluating a graphite structure of a gray cast iron by an image analysis apparatus, comprising the steps of using the image analysis apparatus to perform the steps of:

analyzing a magnified image of the graphite structure, thereby extracting non-spherical graphite pieces of a particular size class contained in the graphite structure to calculate the number and areas of the non-spherical graphite pieces;

calculating a thick and thin degree expressing a degree of thickness of the non-spherical graphite pieces based on the number and the areas; and outputting the number and the thick and thin degree of the non-spherical graphite pieces in combination as an evaluation result, wherein the non-spherical graphite pieces are extracted to calculate the number thereof based on a diameter of a circle having an area equal to that of each graphite piece or on a maximum length of each graphite piece, wherein graphite pieces having a maximum length of 50 μm or more and less than 150 μm are selected from the extracted non-spherical graphite pieces, maximum lengths and areas of the selected graphite pieces are measured, and an area of a graphite piece having a maximum length of 100 μm is calculated based on the measured data and divided by 100, to obtain the thick and thin degree of a representative graphite piece of the graphite structure.

10. A system for quantitatively evaluating a graphite structure of a gray cast iron by image analysis, comprising an image analysis unit, an image input unit for inputting a magnified image of the graphite structure into the image analysis unit, and a display unit for indicating an analysis result, wherein the image analysis unit comprises a graphite piece number/area calculating unit for analyzing the magnified image of the graphite structure to extract non-spherical graphite pieces having sizes within in first range, contained in the graphite structure to calculate a number of the non-spherical graphite pieces, and a thick and thin degree calculating unit for calculating a thick and thin degree expressing a degree of representative thickness of the non-spherical graphite pieces, including a first section for measuring a maximum length and an area of each of the non-spherical graphite pieces having maximum lengths within a second range, included in the extracted non-spherical graphite pieces, a second section for determining an area of a non-graphite piece having a median value of the maximum lengths within the second range depending on the calculated maximum lengths and the areas, and a third section for dividing the determined area by the median value to obtain the thick and thin degree, and the number and the thick and thin degree of the non-spherical graphite pieces are visually indicated on the display unit in combination as an evaluation result.

11. The system for evaluating a graphite structure of a gray cast iron according to claim 10, wherein the smallest graphite piece of the non-spherical graphite pieces extracted to calculate the number thereof has a size of an area equal to that of a circle having a diameter of 5 μm.

12. A system for quantitatively evaluating a graphite structure of a gray cast iron by image analysis, comprising an image analysis unit, an image input unit for inputting a magnified image of the graphite structure into the image analysis unit, and a display unit for indicating an analysis result, wherein the image analysis unit comprises a graphite piece number/area calculating unit for analyzing the magnified image of the graphite structure, thereby extracting non-spherical graphite pieces of a particular size class contained in the graphite structure to calculate the number and areas of the non-spherical graphite pieces, and a thick and thin degree calculating unit for calculating a thick and thin degree expressing a degree of thickness of the non-spherical graphite pieces based on the number and the areas, and the number and the thick and thin degree of the non-spherical graphite pieces are visually indicated on the display unit in combination as an evaluation result, wherein the magnified image is preprocessed to except and eliminate graphite pieces in contact with a frame of the magnified image before extracting the non-spherical graphite pieces of the particular size class, and the image analysis unit comprises a unit for correcting the number of the extracted non-spherical graphite pieces of the particular size class by the steps of counting the graphite pieces to be excepted and eliminated;

classifying graphite pieces other than the graphite pieces to be excepted and eliminated into a plurality of size classes containing the particular size class, to count a number of the other graphite pieces of each size class; and distributing the graphite pieces to be excepted and eliminated into the size classes proportionally based on a ratio between the numbers of the other graphite pieces, to add a number of the distributed graphite pieces to the numbers of the other graphite pieces.

13. A system for quantitatively evaluating a graphite structure of a gray cast iron by image analysis, comprising an image analysis unit, an image input unit for inputting a magnified image of the graphite structure into the image analysis unit, and a display unit for indicating an analysis result wherein the image analysis unit comprises a graphite piece number/area calculating unit for analyzing the magnified image of the graphite structure, thereby extracting non-spherical graphite pieces of a particular size class contained in the graphite structure to calculate the number and areas of the non-spherical graphite pieces, and a thick and thin degree calculating unit for calculating a thick and thin degree expressing a degree of thickness of the non-spherical graphite pieces based on the number and the areas, and the number and the thick and thin degree of the non-spherical graphite pieces are visually indicated on the display unit in combination as an evaluation result, wherein the smallest graphite piece of the non-spherical graphite pieces extracted to calculate the number thereof has a size of an area equal to that of a circle having a diameter of 5 $\mu$m, and wherein graphite pieces having a maximum length of 50 $\mu$m or more and less than 150 $\mu$m are selected from the extracted non-spherical graphite pieces, maximum lengths and areas of the selected graphite pieces are measured, and an area of a graphite piece having a maximum length of 100 $\mu$m is calculated based on the measured data and divided by 100, to obtain the thick and thin degree of a representative graphite piece of the graphite structure.

14. A method for quantitatively evaluating a graphite structure of a gray cast iron by an image analysis apparatus, comprising the steps of using the image analysis apparatus to perform the steps of: analyzing a magnified image of the graphite structure to extract non-spherical graphite pieces contained in the graphite structure to calculate a number of the extracted non-spherical graphite pieces, the extracted non-spherical graphite pieces having at least one of areas each of which is equal to a circle having a diameter of 5 $\mu$m or more and maximum lengths of 10 $\mu$m or more;

calculating a thick and thin degree expressing a representative degree of thickness of the non-spherical graphite pieces, including measuring a maximum length and an area of each of the non-spherical graphite pieces having maximum lengths ranging from 50 $\mu$m or more to less than 150 $\mu$m, included in the extracted non-spherical graphite pieces, determining an area of a non-graphite piece having the maximum length of 100 $\mu$m depending on the calculated maximum lengths and the areas, the maximum length of 100 $\mu$m being a median value of the maximum lengths, and dividing the determined area by 100 to obtain the thick and thin degree; and outputting the calculated number and thick and thin degree of the non-spherical graphite pieces in combination as an evaluation result.

* * * * *